US005723746A

United States Patent [19]
Bestwick et al.

[11] Patent Number: 5,723,746
[45] Date of Patent: Mar. 3, 1998

[54] REDUCED ETHYLENE SYNTHESIS AND DELAYED FRUIT RIPENING IN TRANSGENIC TOMATOES EXPRESSING S-ADENOSYLMETHIONINE HYDROLASE

[75] Inventors: Richard Keith Bestwick, Portland; Adolph J. Ferro, Lake Oswego, both of Oreg.

[73] Assignee: Epitope, Inc., Beaverton, Oreg.

[21] Appl. No.: 46,583

[22] Filed: Apr. 9, 1993

Related U.S. Application Data

[63] Continuation-in-part of Ser. No. 613,858, Dec. 12, 1990, abandoned, which is a continuation-in-part of Ser. No. 448,095, Dec. 12, 1989, abandoned.

[51] Int. Cl.$^6$ .............................. A01H 4/00; A01H 5/08; C12N 15/82; C12N 5/14
[52] U.S. Cl. .............................. 800/205; 800/DIG. 44; 435/172.3; 435/240.4; 435/320.1
[58] Field of Search .............................. 800/205, DIG. 44; 435/240.4, 172.3, 320.1; 536/23.2

[56] References Cited

FOREIGN PATENT DOCUMENTS

WO 91/09112 6/1991 WIPO .
WO 92/12249 7/1992 WIPO .

OTHER PUBLICATIONS

Bestwick, R.K., et al., "Reduced Ethylene Synthesis and Suspended Fruit Ripening in Transgenic Tomatoes Expressing S-Adenosylmethionine Hydrolase." *J. Cell. Biochem. Suppl.* O(18 part A): 98 (1994).

Deikman, J., et al., "Interaction of a DNA binding factor with the 5'-flanking region of an ethylene-responsive fruit ripening gene from tomato." *EMBO J.* 7(11): 3315-3320 (1988).

Deikman, J., et al., "Organization of Ripening and Ethylene Regulatory Regions in a Fruit-Specific Promoter from Tomato (*Lycopersicon esculentum*)." *Plant Physiol.* 100: 2013-2017 (1992).

Giovannoni, J.J., et al., "Expression of a Chimeric Polygalacturonase Gene in Transgenic rin (Ripening Inhibitor) Tomato Fruit Results in Polyuronide Degradation but not Fruit Softening." *Plant Cell* 1: 53-63 (1989).

Langhoff, D.P., et al., "Effect of S-Adenosylmethionine Hydrolase Expression on Ethylene Biosynthesis in Transgenic Tomatoes." *J. Cell. Biochem. Suppl.* O (16 part F): 225 (1992).

Lincoln, J.E., et al., "Regulation of gene expression by ethylene during *Lycopersicon esculentum* (tomato) fruit development." *Proc. Natl. Acad. Sci. USA* 84: 2793-2797 (1987).

Deikman et al. (1988) The EMBO Journal vol. 7 (11), pp. 3315-3320.

Boswell et al. in Computational Molecular Biology Sources and Methods for Sequence Analysis (Lesk, ed.) Oxford University Press, Oxford, 1988, pp. 170-171.

U.S. application No. 08/255,833, Ferro et al., filed Jun. 8, 1994.

Hamilton, et al. (Jul. 1990) Nature 346:284-287.

Tigchelaar, et al. (Oral Disclosure Mar. 1988, Written Disclosure 1989) in (Griggs, et al. eds) Tomato and Pepper Production in the Tropics: International Symposium on Integrated Management Practices, Taiwan, pp. 123-136.

Gelvin (1987) Plant Molecular Biology 8: 355-359.

Vaeck, et al. (Jul. 1987) Nature 328: 33-37.

Fischhoff, et al. (1987) Bio/Technology 5: 807-813.

*Primary Examiner*—Che S. Chereskin
*Attorney, Agent, or Firm*—Susan T. Evans; Gary R. Fabian

[57] ABSTRACT

The use of AdoMetase to reduce ethylene biosynthesis in plants is facilitated by the exploitation of the tissue and stage specific properties of the E8 promoter from tomato. Expression of AdoMetase is shown to be limited to the ripening tomato fruit. The functional properties of several regions of the E8 promoter are also described. The E8 promoter, and variants described herein, provides a useful regulatable promoter for the expression of other genes as well as the AdoMetase gene.

35 Claims, 21 Drawing Sheets

1124bp E8 promoter fragment used in first generation SAMase tomatoes

3' primer  NcoI
ATTCACAGTGCAAAGACCATGGAA

5' primer
GGTCTAGAAGGAATTTCACG

XbaI (-1124bp)

HindIII (-2254 bp)

Tomato E8 gene

2254bp enhanced SE8 promoter fragment

Fig. 3

Fig. 11A pUC19SAM-K

```
                                                                              XhoII
                                                                              Sau3AI
                                                                              NlaIV
                                                                  TaqI        NdeII
                                                                  SalI  XbaI  MboI
                                                                  MnlI         CpfI
                                                           PstI HinfI          BstI
                               HindIII                     HincII  AccI  MaeI BamHI
                               EcoVIII  SphI               ||      |     |    |
          NlaIII               AluI     NlaIII
AluI      |                    |        |                  ||
|         |
1 ACAGCTATGACCATGATTACGCCAAGCTTGCATGCCTGCAGGTCGACTCTAGAGGATCC MnlI     MnlI                          HphI                   NlaIII
            |        |                             |                      |
115 CTTTCCGTTCTAACCTCTGCGATGAGGTGAATATGAGCAGACACCGCCACATGGTAAGC
    laPheArgSerAsnLeuCysAspGluValAsnMETSerArgHisArgHisMETValSer MnlI
    HinPlI
    HhaI                                    RsaI
    CfoI  DdeI                              |
    |||   |
235 ATCGTGAGGCAATCTCAAGCGCCACCAACTGAGGAAAAAACTGTTCGTGTACGCTACAAG
    yrArgGluAlaIleSerSerAlaProThrGluGluLysThrValArgValArgTyrLys
```

Fig. 11B

```
                    XmnI
            MboII   Asp700       RsaI
NcoI          -       -            -
GCCACCATGGTTTCACTAAAGAGCCTGCGAACGTCTTCTATGTACTGGTTTCCG 114
 METValPheThrLysGluProAlaAsnValPheTyrValLeuValSerA

ScrFI
          ScrFI                                           NclI
          NclI                                            MspI
          MspI                            HinfI           HpaII   MnlI
    Fnu4HI HpaII            NlaIV           -    HincII     -       -
      -     -                 -                              
ACTTTACGTGCCGCCACCGGGTCTCTTTATGGCTCCGTTGAGTCAACCGATTTGACCGGTGCT 234
 ThrLeuArgAlaAlaProGlyLeuTyrGlySerValGluSerThrAspLeuThrGlyCysT HinP1I
HhaI      MaeI
Fnu4HI    AluI
CfoI  BbvI  -
 ||    -
GACAAAGCCAGGCACTCAATGTTGCACGCCTAGTCTTGTAATGAGTGGGAGCAAGATTGCG 354
 AspLysAlaGlnAlaLeuAsnValAlaArgLeuAlaCysAsnGluTrpGluGlnAspCysV
```

```
      RsaI  AccI         HinfI                                      RsaI                          TaqI
       —    —             —                                          —                             —
355 TACTGGTATACAAATCACAGACTCACACGGCTGGTCTGGTACGCTAAAGGTATCGAC
    aLeuValTyrLysSerGlnThrHisThrAlaGlyLeuValTyrAlaLysGlyIleAsp Fnu4HI              Fnu4HI    RsaI
       —                   —        —
474 AAGGCTGCTTCACTATTGATGAGTTCGGTCGCCCGCTGGCAAGTACAATAAGTGTTAAAC
    lnGlyCysPheThrIleAspGluPheGlyArgArgTrpGlnValGln***
```

Fig. 11C

```
                                                                    HinP1I
                                                                    HhaI
                                                                    CfoI
                                         NlaIV                      BbvI    Fnu4HI
             ScrFI                       BbvI                        |       |
             NcII                         |                          |       |
             MspI                         |                          |       |
             HpaII  MnlI                  |                          |       |
              ||     |                    |                          |       |
GGGTATAAGGCTGAACGTCTGCCGGGTAGTTTCCAAGAGGTTCCTAAAGGCGCACCGCTGC 474
GlyTyrLysAlaGluArgLeuProGlySerPheGlnGluValProLysGlyAlaProLeuG

TaqI
                                         SstI
                                         SacI
                         RsaI            HglAI
                         NlaIV           EcoRI
                  Sau3AI KpnI            BanII
                  NdeII   |               |
                  MboI BanI               |
                  CpfI Asp718 AluI        |    BanI
SfaNI NlaIII        |    |    |           |     |
  |     |           |    |    |           |     |
TCAAGGTCATGCACGATGCGTGGCCGGATCGGGTACCGAGCTCGAATTCACTGG 586
```

Fig. 11D

```
Sequence Range: 1 to 2216
>EcoR1

|     10          20          30          40          50          60          70
     GAATTCATTT  TTGACATCCC  TAATGATATT  GTTCACGTAA  TTAAGTTTTG  TGGAAGTGAG  AGAGTCCAAT 80          90         100         110         120         130         140
     TTTGATAAGA  AAAGAGTCAG  AAAACGTAAT  ATTTTAAAAG  TCTAAATCTT  TCTACAAATA  AGAGCAAATT 150         160         170         180         190         200         210
     TATTTATTTT  TTAATCCAAT  AAATATTAAT  GGAGGACAAA  TTCAATTCAC  TTGGTTGTAA  AATAAACTTA 220         230         240         250         260         270         280
     AACCAATAAC  CAAAGANCTA  ATAAATCTGA  AGTGGAATTA  TTAAGGATAA  TGTACATAGA  CAATGAAGAA 290         300         310         320         330         340         350
     ATAATAGGTT  CGATGAATTA  ATAATAATTA  AGGATGTTAC  AATCATCATG  TGCCAAGTAT  ATACACAATA 360         370         380         390         400         410         420
     TTCTATGGGA  TTTATAATTT  CGTTACTTCA  CTTAACTTTT  GCGTAAATAA  AACGAATTAT  CTGATATTTT 430         440         450         460         470         480         490
     ATAATAAAAC  AGTTAATTAA  GAACCATCAT  TTTTAACAAC  ATAGATATAT  TATTTCTAAT  AGTTTAATGA 500         510         520         530         540         550         560
     TACTTTTAAA  TCTTTTAAAT  TTTATGTTTC  TTTTAGAAAA  TAAAAATTCA  AAAAAATTAA  ATATATTTAC 570         580         590         600         610         620         630
     AAAAACTACA  ATCAAACACA  ACTTCATATA  TTAAAAGCAA  AATATATTTT  GAAAATTTCA  AGTGTCCTAA 640         650         660         670         680         690         700
     CAAATAAGAC  AAGAGGAAAA  TGTACGATGA  GAGACATAAA  GAGAACTAAT  AATTGAGGAG  TCCTATAATA 710         720         730         740         750         760         770
     TATAATAAAG  TTTATTAGTA  AACTTAATTA  TTAAGGACTC  CTAAAATATA  TGATAGGAGA  AAATGAATGG 780         790         800         810         820         830         840
     TGAGAGATAT  TGGAAAACTT  AATAATTAAG  GATNTTAAAA  TATATGGTAA  AAGATAGGCA  AAGTATCCAT 850         860         870         880         890         900         910
     TATCCCCTTT  TAACTTGAAG  TCTACCTAGG  CGCATGTGAA  AGGTTGATTT  TTTGTCACGT  CATATAGCTA 920         930         940         950         960         970         980
     TAACGTAAAA  AAAGAAAGTA  AAATTTTTAA  TTTTTTTTAA  TATATGACAT  ATTTAAACG   AAATATAGGA 990        1000        1010        1020        1030        1040        1050
     CAAAATGTAA  ATGAATAGTA  AAGGAAACAA  AGATTAATAC  TTACTTTGTA  AGAATTTAAG  ATAAATTTAA

>Xbal                   >Xbal
                            |                       |
          1060        1070  |     1080        1090  |     1100        1110        1120
     AATTTAATAG  ATCAACTTTA  CGTCTAGAAA  GACCCATATC  TAGAAGGAAT  TTCACGAAAT  CGGCCCTTAT 1130        1140        1150        1160        1170        1180        1190
     TCAAAAATAA  CTTTTAAATA  ATGAATTTTA  AATTTAAGA   AATAATATCC  AATGAATAAA  TGACATGTAG
```

Fig. 13A

```
        1200       1210       1220       1230       1240       1250       1260
CATTTTACCT AAATATTTCA ACTATTTTAA TCCAATATTA ATTTGTTTTA TTCCCAACAA TAGAAAGTCT 1270       1280       1290       1300       1310    |  1320       1330
TGTGCAGACA TTTAATCTGA CTTTTCCAGT ACTAAATATT AATTTTCTGA AGATTTTCGG GTTTAGTCCA 1340       1350       1360       1370       1380       1390       1400
CAAGTTTTAG TGAGAAGTTT TGCTCAAAAT TTTAGGTGAG AAGGTTTGAT ATTTATCTTT TGTTAAATTA 1410       1420       1430       1440       1450       1460       1470
ATTTATCTAG GTGACTATTA TTTATTTAAG TAGAAATTCA TATCATTACT TTTGCCAACT TGTAGTCATA 1480       1490       1500       1510       1520       1530       1540
ATAGGAGTAG GTGTATATGA TGAAGGAATA AACAAGTTCA GTGAAGTGAT TAAAATAAAA TATAATTTAG 1550       1560       1570       1580       1590       1600       1610
GTGTACATCA AATAAAAACC TTAAAGTTTA GAAAGGCACC GAATAATTTT GCATAGAAGA TATTAGTAAA 1620       1630       1640       1650       1660       1670       1680
TTTATAAAAA TAAAAGAAAT GTAGTTGTCA AGTTGTCTTC TTTTTTTTGG ATAAAAATAG CAGTTGGCTT 1690       1700       1710       1720       1730       1740       1750
ATGTCATTCT TTTACAACCT CCATGCCACT TGTCCAATTG TTGACACTTA ACTAATTAGT TTGATTCATG 1760       1770       1780       1790       1800       1810       1820
TATGAATACT AAATAATTTT TTAGGACTGA CTCAAATATT TTTATATTAT CATAGTAATA TTTATCTAAT 1830       1840       1850       1860       1870       1880       1890
TTTTAGGACC ACTTATTACT AAATAATAAA TTAACTACTA CTATATTATT GTTGTGAAAC AACAACGTTT 1900       1910       1920       1930       1940       1950       1960
TGGTTGTTAT GATGAAACGT ACACTATATC AGTATGAAAA ATTCAAAACG ATTAGTATAA ATTATATTGA 1970       1980       1990       2000       2010       2020       2030
AAATTTGATA TTTTTCTATT CTTAATCAGA CGTATTGGGT TTCATATTTT AAAAAGGGAC TAAACTTAGA 2040       2050       2060       2070       2080       2090       2100
AGAGAAGTTT GTTTGAAACT ACTTTTGTCT CTTTCTTGTT CCCATTTCTC TCTTAGATTT CAAAAAGTGA
|
        2110       2120       2130       2140       2150       2160    |  2170
        *          *          *          *          *          *       |     *
ACTACTTTAT CTCTTTCTTT GTTCACATTT TATTTTATTC TATTATAAAT ATGGCATCCT CATATTGAGA

>Xmn1                            >Nco1
           |                           >E8_Start_codon
           |          |                     |  |
        2180 |     2190 |     2200       2210  |
           * |        * |        *          |* |
TTTTTAGAAA TTATTCTAAT CATTCACAGT GCAAAGACC ATGGAA
```

Fig. 13B

REDUCED ETHYLENE SYNTHESIS AND DELAYED FRUIT RIPENING IN TRANSGENIC TOMATOES EXPRESSING S-ADENOSYLMETHIONINE HYDROLASE

This application is a continuation-in-part of co-owned, U.S. patent application Ser. No. 07/613,858, filed 12, Dec. 1990, now abandoned, which is a continuation-in-part of U.S. patent application Ser. No. 448,095 filed Dec. 12, 1989, now abandoned.

FIELD OF THE INVENTION

The present invention describes the use of S-adenosylmethionine hydrolase to reduce ethylene biosynthesis in plants, where expression of an S-adenosylmethionine hydrolase encoding gene is under the control of a tissue and stage specific promoter.

REFERENCES

Ausubel, F. M., et al., *Current Protocols in Molecular Biology*, John Wiley and Sons, Inc., Media PA.

Adams, D. O., et al., *Plant Physiol.* 70:117–123 (1977).

An, G., et al., *EMBO J.* 4:277–284 (1985).

An, et al., "Binary Vectors" in *Plant Molecular Biology Manual* A3:1–19 (1988).

Bellini, C., et al., *Bio/Technol* 7(5):503–508 (1989).

Deikman, J., et al., *EMBO J.* 7:3315 (1988).

Deikman, J., et al., *Plant Physiol.* 100:2013 (1992).

Fillatti, J. J., et al., *Biotechnology* 5:726 (1987).

Fritsch, E. F., et al., in *Molecular Cloning: A Laboratory Manual* (Cold Spring Harbor Lab., Cold Spring Harbor, N.Y.), 2nd Ed. (1989).

Giovannoni, J. J., et al., *Plant Cell* 1:53–63 (1989).

Hamilton, A. J., et al., *Nature* 346:284 (1990).

Hood, E., et al., *J. Bacteriol.* 168:1291–1301 (1986).

Hughes, J. A., et al., *J. Bact.* 169:3625 (1987a).

Hughes, J. A., et al., *Nuc. Acid. Res.* 15:717 (1987b).

Horsten, K. H., et al., *J. Gert. Virol.* 43:57–73 (1979).

Imaseki, H., "The Biochemistry of Ethylene Biosynthesis", in *The Plant Hormone Ethylene* (Mattoo, A. K., et al., eds.) CRC Press, pp 1–20 (1991).

Klee, H. J., et al., *The Plant Cell* 3:1187–1193 (1991).

Klein, T. M., et al., *PNAS* (USA) 85 (22):8502–8505 (1988).

Kozak, M., *J. Mol. Bio.* 196:947 (1987).

Kushad, M. M., et al., *Plant Physiol.* 73:257–261 (1983).

Lee, J. J., et al., *Methods in Enzymology* 152:633–648 (1987).

Lincoln, J. E., et al., *Proc. Natl. Acad. Sci. USA* 84:2793 (1987).

Lutcke, H. A., et al., *EMBO J.* 6:43–48 (1987).

Maniatis, T., et al. *Molecular Cloning: A Laboratory Manual*, Cold Spring Harbor Laboratory (1982).

Mertens, H., et al., *J. Gen. Virol.* 62:331–341 (1982).

Miki, B. L. A., et al., *Plant DNA Infectious Agents* (Hohn, T., et al., eds.) Springer-Verlag, Wien, Austria, pp.249–265 (1987).

Mullis, K. B., U.S. Pat. No. 4,683,202, issued Jul. 28, 1987.

Mullis, K. B., et al., U. S. Pat. No. 4,683,195, issued 28, Jul. 1987.

Nagel, R., et al., FEMS *Microbiol. Lett.* 67:325 (1990).

Oeller, P. W., et al., *Science* 254:437–439 (1991).

Sambrook, J., et al., In *Molecular Cloning: A Laboratory Manual*, Cold Spring Harbor Laboratory Press, Vol. 2 (1989).

Studier, F. W., et al., *J. Virol* 19:136 (1976).

BACKGROUND OF THE INVENTION

Ethylene is a plant hormone which is a powerful regulator of plant metabolism, acting, and interacting with other plant hormones in trace amounts. Ethylene is a gas under normal physiological conditions. Even at low concentrations, ethylene has profound hormonal effects on plants.

The effects of ethylene, whether produced by the plant itself or applied exogenously, are numerous, dramatic, and of considerable commercial importance. Among the diverse physiological effects are the following: leaf abscission; fading in flowers; flower wilting; leaf yellowing; leaf epinasty; and stimulation of ripening in fruits and vegetables. Ethylene promotes senescence in plants, both in selected groups of cells and in whole organs, such as, fruits, leaves, or flowers. Senescence is the natural, genetically controlled degenerative process which usually leads to death in plants.

Normally, ethylene production from plant tissue is low. Large quantities of ethylene, however, are produced during ripening and senescence processes. A large amount of ethylene is also produced following trauma caused by chemicals, temperature extremes, water stress, ultraviolet light, insect damage, disease, or mechanical wounding. Ethylene produced by plants under such trauma conditions is referred to as "wound ethylene" or "stress ethylene". In fruits and vegetables, the stimulation of ethylene production by cuts or bruises may be very large and bear considerably on storage effectiveness. Ethylene-induced leaf browning is a common basis for loss in many plants, including lettuce and tobacco. In some tissues, exposure to only a small amount of ethylene may cause an avalanche of ethylene production in adjacent plants or plant tissues such as fresh produce. This autocatalytic effect can be very pronounced and lead to loss of fruit quality during transportation and storage.

Current technologies that specifically address post-harvest storage life have been in existence for decades and are hampered by such problems as high cost, side effects, and an inability to completely shut off ethylene production. Included in this group are controlled atmosphere (CA) storage, chemical treatment, packaging, and irradiation.

CA facilities slow ethylene biosynthesis through: (i) low temperature, (ii) reducing the oxygen level below 3%, and (iii) elevating the carbon dioxide level in the storage area to the 3%–5% range. Expensive scrubbers are sometimes added which reduce ethylene already respired to the atmosphere. Drawbacks are that CA facilities are expensive to construct, have a high utility cost, and are unable to completely eliminate ethylene production and side effects. Also, CA storage techniques can only control external ethylene and not that which resides inside the plant tissue. CA storage can also lead to undesirable side effects: injury can result from high $CO_2$ levels, low $O_2$ levels, or low temperature.

Another treatment is to limit the ethylene biosynthesis in the plant tissue through chemical treatment. Aminoethoxyinylglycine (AVG), an analog of the antibiotic rhizobitoxine, is one such inhibitor. However, AVG cannot be used as a chemical additive in foods due to its high toxicity. Silver thiosulfate (STS) is also effective in slowing fruit ripening and flower fading, but is also toxic and cannot be used on foods. Further, STS only works with certain flowers and often causes black spotting.

Recently, molecular genetic approaches leading to transgenic plants with impaired biosynthesis of ethylene have been reported. Hamilton, et al., identified a cDNA clone for tomato EFE (pTOM13) by inhibiting ethylene synthesis with an antisense gene expressed in transgenic plants. Oeller, et al., showed that expression of antisense RNA to the rate-limiting enzyme in the biosynthetic pathway of ethylene, 1-aminocyclopropane-1-carboxylate synthase, inhibits fruit ripening in tomato plants. Klee, et al., cloned the gene encoding ACC deaminase, from soil bacteria, and introduced it into tomato plants. Reduction in ethylene synthesis in transgenic plants did not cause any apparent vegetative phenotypic abnormalities. However, fruits from these plants exhibited significant delays in ripening, and the mature fruits remained firm for at least 6 weeks longer than the non-transgenic control fruit.

SUMMARY OF THE INVENTION

The present invention describes the development of transgenic fruit-bearing plants. These plants contain a DNA sequence which encodes and expresses a S-adenosylmethionine hydrolase enzyme (AdoMetase). This enzyme is capable of hydrolyzing S-adenosylmethionine to homoserine and 5'-methylthioadenosine. In these plants the expression of the AdoMetase sequence is under the transcriptional control of an E8 promoter.

The E8 gene promoter comprises the regulatory region located 5' to the coding sequence of the tomato E8 gene. Promoters homologous to the E8 promoter can be identified by standard hybridization or DNA amplification methods. FIGS. 13A and 13B present a representative nucleotide sequence of a portion of the E8 promoter. Two E8 promoter regions have been defined by the present invention, the SE8 promoter, which includes the entire region represented in FIGS. 13A and 13B, and the lower E8 promoter, which includes the region represented as bases 1090 to 2214. Either of these promoters can be used in generating the transgenic plants of the present invention.

The AdoMetase enzyme coding sequence can be obtained from a number of bacteriophage including the following: *Escherichia coli* bacteriophage T3, coliphage BA14, *Klebsiella* phage K11, and *Seratti* phage IV. An exemplary AdoMetase enzyme coding sequence was derived from *Escherichia coli* bacteriophage T3 and a representative coding sequence is presented in FIGS. 11A to 11D.

One embodiment of the present invention is a transgenic tomato plant. The invention also includes transgenic tomato-fruit cells containing a DNA sequence which encodes and expresses a AdoMetase, where expression of AdoMetase is under the transcriptional control of an E8 promoter.

The present invention also includes a method for reducing ethylene biosynthesis in fruit cells of a plant. In this method a vector is provided containing a first DNA sequence containing a gene useful for genetic selection in plant cells, where this sequence is flanked by regulatory elements effective to allow expression of the sequence in plant host cells. The vector also includes a second DNA sequence which (i) is flanked by regulatory elements effective to allow expression of the sequence in plant fruit cells, (ii) encodes a S-adenosylmethionine hydrolase enzyme which hydrolyses S-adenosylmethionine to homoserine and 5'-methylthioadenosine. This vector is used to transform plant host cells. These cells are cultivated to generate transgenic plants. When the transgenic plants bear fruit, the fruit cells are capable of expressing the AdoMetase enzyme.

The AdoMetase enzyme coding sequences can be obtained from the same sources as described above.

The vector can be introduced into host plant cells by a number of transformation methods including, Agrobacterium-mediated transformation, electroporation, microinjection, and microprojectile bombardment. A typical gene useful for genetic selection in plant cells is a gene which confers kanamycin resistance.

Expression of the AdoMetase gene can be regulated by a tissue or stage specific promoter, including an E8 promoter, or derivatives thereof.

The invention further includes vectors useful in the transformation method of the present invention. Such vectors typically include a duplex DNA fragment containing a DNA sequence which encodes a S-adenosylmethionine hydrolase enzyme and, adjacent this sequence, an E8 promoter, or derivative thereof.

The invention also includes the use of variants of the E8 promoter, described herein, to confer tissue and/or stage specific expression to any gene placed under their control.

BRIEF DESCRIPTION OF THE FIGURES

FIG. 3 illustrates the elements of the tomato E8 promoter and the primers used to amplify and isolate the promoter sequences.

FIG. 9C, ES 35-1; and FIG. 9D, ES22 A-1) over a ten day period after entry of the fruit into breaker stage.

FIGS. 11A–11D present the sequence of the SAM-K modification of the AdoMetase gene derived from bacteriophage T3.

FIGS. 13A and 13B present the sequence of the upstream minus 2216 base pair region of the tomato E8 gene.

DETAILED DESCRIPTION OF THE INVENTION

The present application describes a method for the inhibition of ethylene biosynthesis in plants which is a modification of the method described in co-owned, co-pending U.S. application Ser. No. 07/613,858, filed 12, Dec. 1990, herein incorporated by reference.

I. Use of S-Adenosylmethionine Hydrolase in Plants.

The amino acid methionine has been shown to be a precursor of ethylene in plant tissues (reviewed by Imaseki). Methionine, however, is not the immediate precursor but first must be converted to the sulfonium compound S-adenosylmethionine (SAM) and, subsequently, aminocyclopropane-1-carboxylic acid (ACC) prior to conversion to ethylene. The metabolic reactions for the synthesis of ethylene from methionine under both normal and stress conditions are presented in FIGS. 1A and 1B and summarized as follows:

Methionine→SAM→ACC→Ethylene

ACC synthase catalyzes the degradation of SAM to ACC and 5'-methylthioadenosine (MTA). This enzymatic reaction appears to be the rate limiting step in ethylene formation. For example, the natural plant hormone indoleacetic acid (IAA or auxin) stimulates ethylene production by inducing the synthesis of ACC synthase. Conversely, the synthesis of SAM from methionine and the production of ethylene from ACC do not require auxin induction.

Figure 1A:
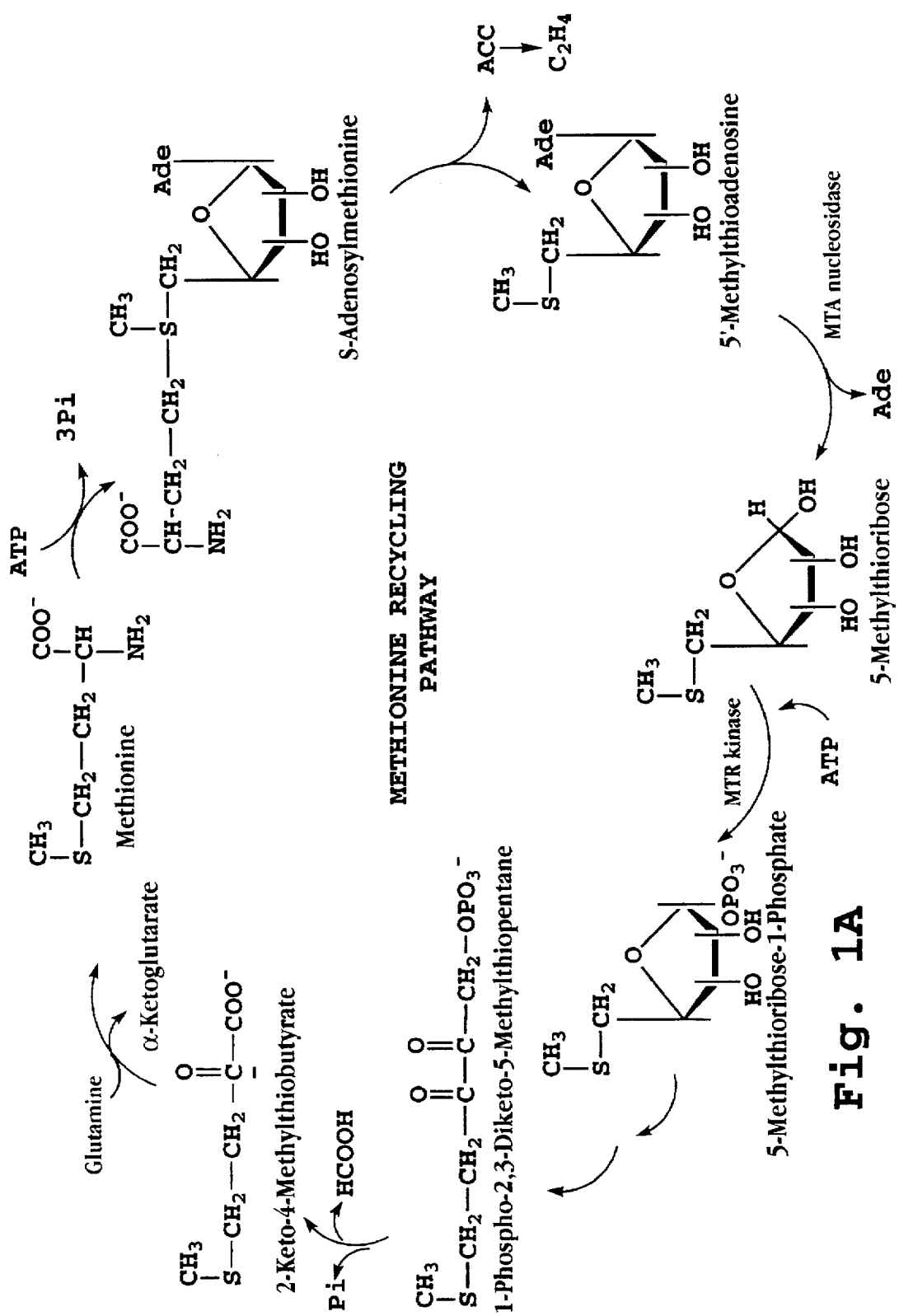
FIGS. 1A and 1B schematically illustrate the metabolic reactions for the synthesis of ethylebe from methionine. The effect AdoMetase expression in plant cells has on the plant methionine recycling pathway is shown schematically in FIG. 1B.

In addition, wounding and fruit ripening induces the formation of ACC synthase and, therefore, the conversion of SAM to ACC. The other product of the ACC synthase reaction, MTA, must be recycled back into methionine so as to provide an adequate supply of methionine for continual ethylene production. This recycling pathway from MTA to methionine has been shown to exist in plant tissue (Adams, et al.; Kushad, et al.). The degradation of MTA has added significance in light of the finding that MTA is a potent inhibitor of ACC synthase. The importance of the degradation and recycling of MTA in normal plant tissues is, therefore, twofold: 1) to prevent the direct inhibition of ethylene synthesis by MTA, and 2) to provide adequate methionine for continual ethylene synthesis. A summary of this metabolic pathway is shown in FIG. 1A.

The first step in the degradation of MTA in plant tissue is the hydrolysis of this nucleoside to 5-methylthioribose (MTR) by a specific MTA nucleosidase. MTR not only provides its methylthio moiety for the formation of methionine, but also contributes four carbons from its ribose towards the synthesis of this amino acid. Therefore, the methylthio group is conserved by recycling. It should be noted that this pathway merely maintains a methionine supply for ethylene biosynthesis, but does not result in a net increase in methionine synthesis.

The approach to reduce ethylene biosynthesis in plants reported here and in parent application U.S. patent application Ser. No. 07/613,858, filed 12, Dec. 1990, utilizes a gene that encodes the enzyme S-adenosylmethionine hydrolase. This enzyme, encoded by the *E. coli* bacteriophage T3, hydrolyses AdoMet to homoserine and MTA. The enzyme is known as its recommended name, AdoMet hydrolase (AdoMetase), or by its other name, S-adenosylmethionine cleaving enzyme (SAMase) (Studier, et al.). Both products of the reaction (i.e., homoserine and MTA) are recycled to methionine; MTA as previously shown (FIG. 1B) and homoserine via a metabolism pathway known to exist in plant tissues.

The AdoMetase gene has been identified, isolated, cloned, and sequenced (Hughes, et al., 1987a; Hughes, et al., 1987b). The gene contains two in-frame reading sequences that specify polypeptides of 17105 and 13978 daltons. Both polypeptides terminate at the same ochre codon. This results in the 14 kd polypeptide being identical to 82% of the 17 kd polypeptide starting at the carboxyl end of the longer polypeptide. Both polypeptides are present in partially purified cells and from *E. coli* expressing the cloned gene (Hughes, et al., 1987b; Studier, et al., 1976). Other bacteriophages that encode the AdoMetase or SAMase genes are coliphage BA14, Klebsiella phage K11, and Serratia phage IV (Mertens, et al.; Horsten, et al.).

Figure 1B:
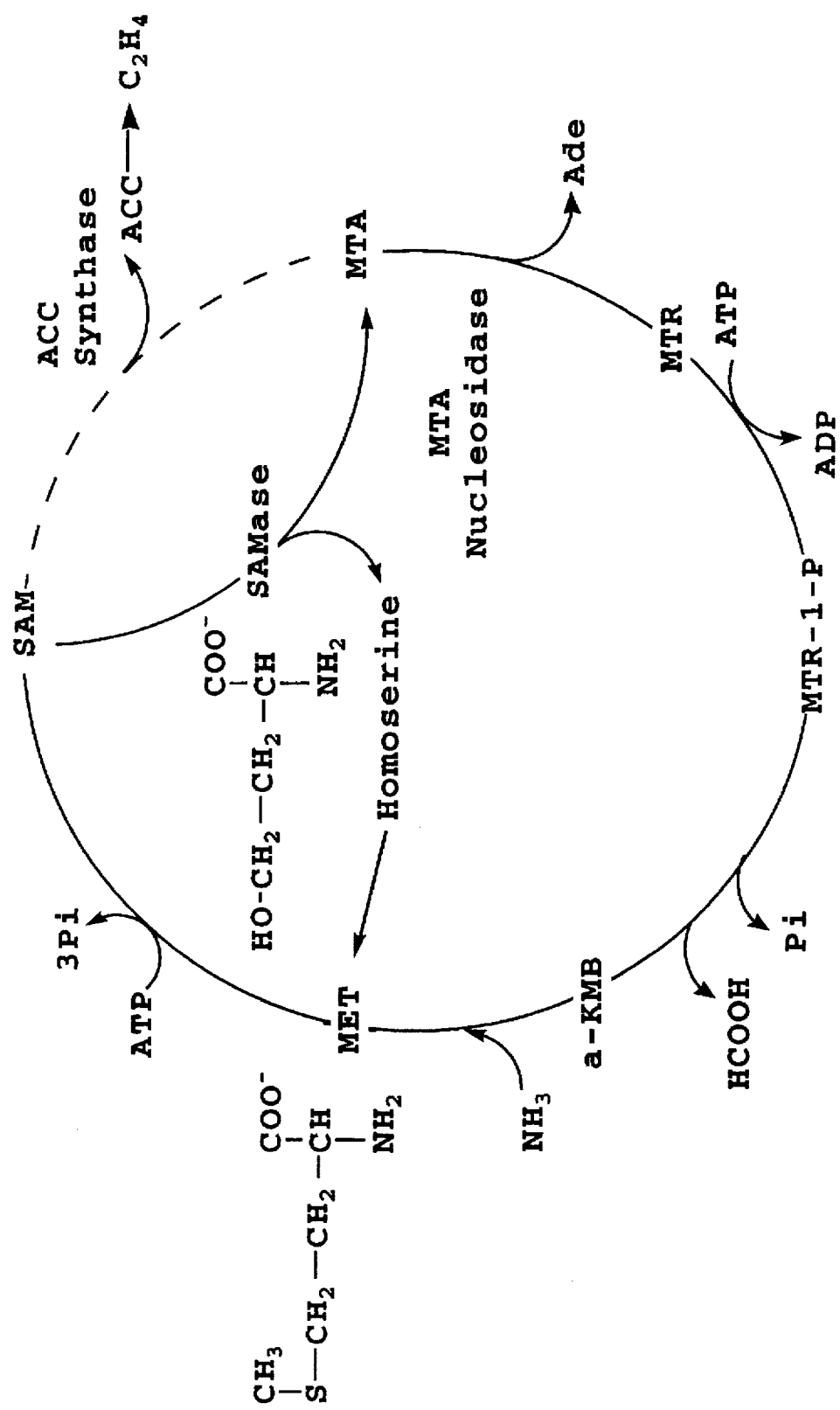

The effect AdoMetase expression in plant cells has on the plant methionine recycling pathway is shown schematically in FIG. 1B. Experiments performed in support of the present invention, using transgenic plants expressing an AdoMetase gene and monitoring ethylene production, have demonstrated that the effect of AdoMetase on the pathway is to "short circuit" the branch that produces ethylene: ethylene production is reduced in such transgenic plants, including production in leaf tissue and fruit.

II. AdoMetase Encoding Genes.

Different bacteriophages may be expected to contain AdoMetase genes with variations in their DNA sequences. The isolation of AdoMetase coding sequences from bacteriophage coding sequences can be accomplished as previously described for AdoMetase from bacteriophage T3. Alternatively, degenerative hybridization probes for AdoMetase coding sequences can be generated and used to screen plasmids carrying fragments of a selected bacteriophage's genome for the presence of homologous sequences. AdoMetase enzymatic activity can be evaluated by standard biochemical tests (see for example, Example 5).

Furthermore, the amino acid sequence of AdoMetase may be modified by genetic techniques to produce enzymes with altered biological activities (see below). An increase in the biological activity could permit the use of lower amounts of the enzyme to control ethylene biosynthesis in plants.

Figure 2:
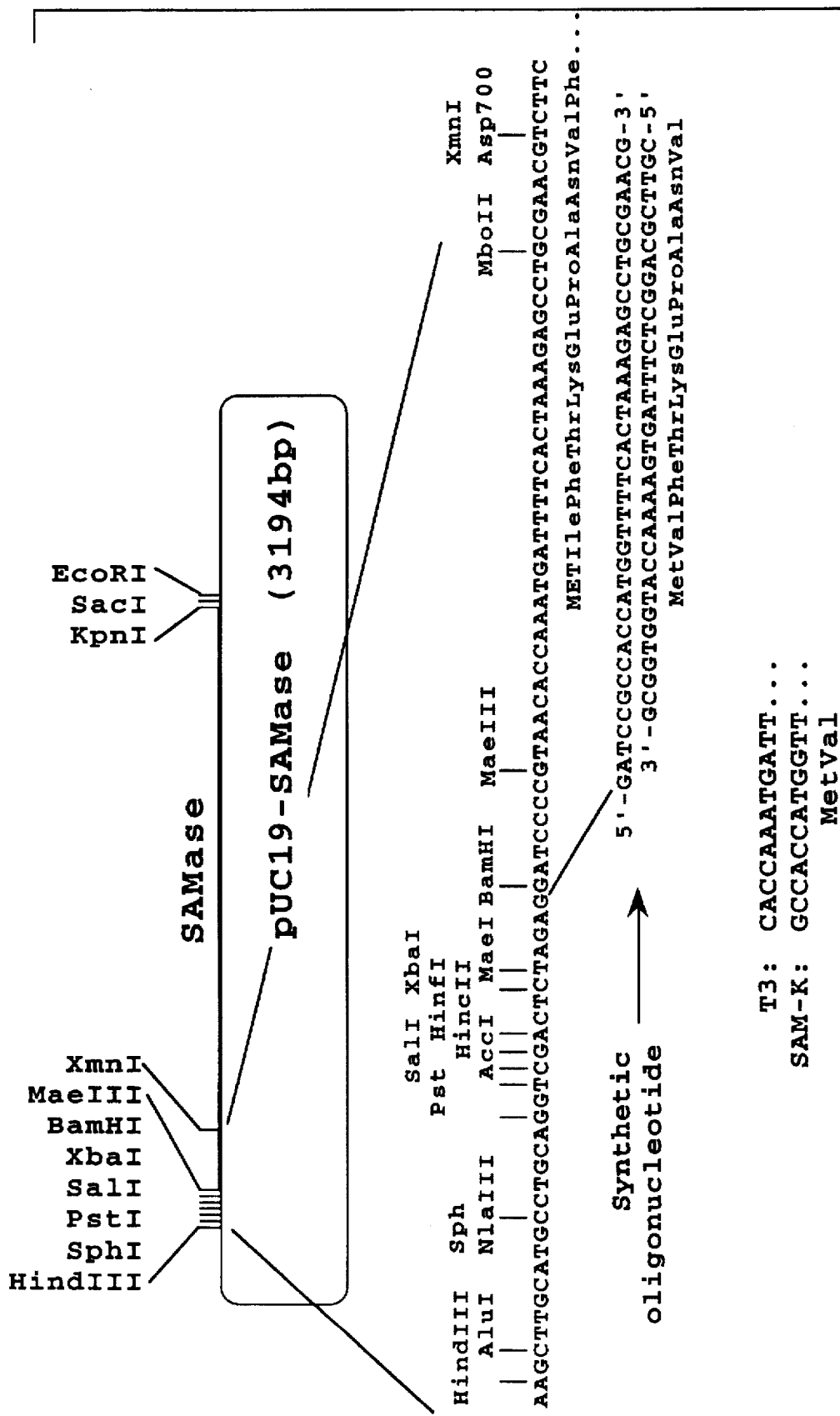
FIG. 2 schematically illustrates the steps described for the genetic engineering of the AdoMetase-encoding gene.

A series of recombinant DNA manipulations were performed in the AdoMetase gene prior to placement in an Agrobacterium expression vector. Initially, a MaeIII to BamHI fragment from M13HB1 (Hughes, et al., 1987a) was subcloned into the pUC19 plasmid vector to produce pUC19-SAM (Example 1). To increase the translational efficiency of the AdoMetase gene in plants, site directed mutagenesis of the nucleic acid sequences surrounding the ATG start codon was performed. A synthetic double stranded 39 base pair oligonucleotide was synthesized by annealing single-stranded oligonucleotides represented by SEQ ID NO:3 and SEQ ID NO:5 and substituted for the BamHI to XmnI fragment at the 5' end of the gene (FIG. 2). The net effect of this substitution was to change the CAC-CAA<u>ATG</u>A in the native T3 sequence to GCCACC<u>ATGG</u> which an optimal eukaryotic translational initiation sequence (Kozak, et al.; Lutcke, et al.).

The change also introduces an NcoI site (CCATGG) at the SAMase start codon which facilitates fusions to different promoters. The only alteration to the AdoMetase coding sequence is the amino acid at amino acid position two which is changed from isoleucine to valine: this is a highly conservative amino acid change. The altered form of AdoMetase was named SAM-K FIGS. 11–11D.

A recombinant vaccinia vector with SAM-K (vv:SAM-K) was constructed. Expression of this vector in African green monkey cells or T3-infected bacterial cells was compared with the gene to the native T3 gene when expressed in the same cells. The specific activity of AdoMetase was higher in the vv:SAM-K infected cells than in the T3 infected bacterial cells demonstrating that SAM-K encodes a fully functional version of AdoMetase.

Experiments performed in support of the present invention have demonstrated constitutive expression of AdoMetase in transgenic tomato and tobacco plants. In these plants there was a significant reduction in the ability of these plants to synthesize ethylene as measured in a leaf disk assay.

III. Promoter Regulated SAMase Gene Expression.

Regulatable promoters have been employed in the method of the present invention. One exemplary regulatable promoter is the tomato E8 gene promoter. Expression of the E8 gene has been shown to be induced (i) at the onset of ripening, and (ii) by treatment of tomatoes with ethylene (Deikman, et al., 1988; Lincoln, et al.; Giovannoni, et al.). The sequence of the E8 promoter has been published (Deikman, et al., 1988; Deikman, et al., 1992) and the DNA sequence of the minus 2216 base pair region is presented in FIGS. 13A and 13B (SEQ ID NO:12

Using the sequence shown in FIGS. 13A and 13B primers were prepared for use in the polymerase chain reaction (PCR) to amplify the 1124 base pair promoter from tomato genomic DNA (Example 1). The primers represented by SEQ ID NO:8 and SEQ ID NO:9, were designed with unique restriction sites at each end and were used to place the promoter in the proper orientation 5' of the SAM-K gene in pUC19 (FIG. 3). The 35' end of the promoter fragment had an NcoI site (CCATGG) placed such that the ATG start codon of the E8 gene product was used as the ATG in the NcoI site. This allowed precise placement of the entire E8 promoter directly in front of the SAM-K amino acid coding sequences with no intervening sequences (Example 1, FIGS. 12A, 12B, and 12C.

Figure 4:
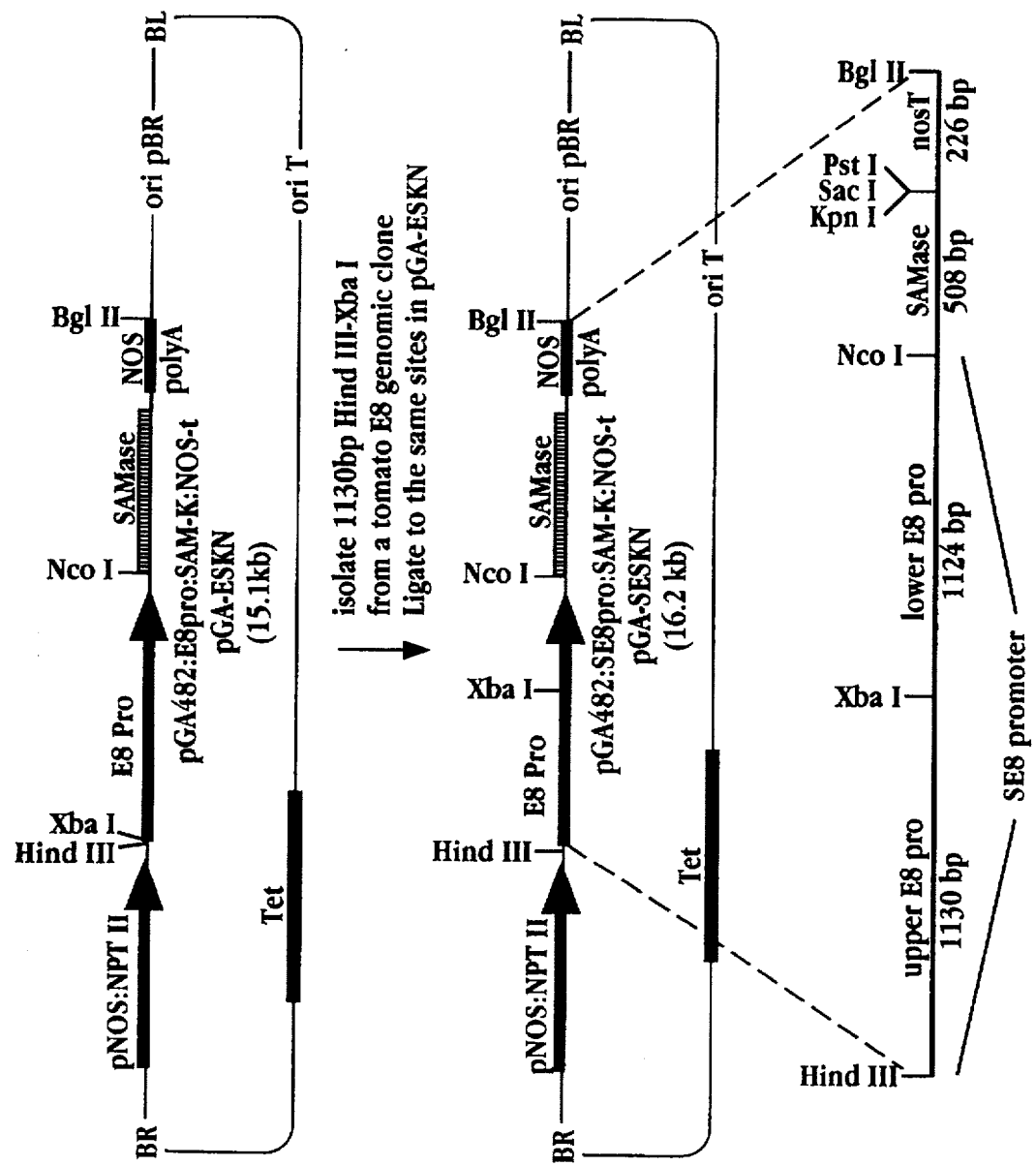
FIG. 4 outlines the steps involved in the construction of pGA-SESKN from pGA-ESKN and shows the elements of the E8 gene adjacent the AdoMetase (SAMase) coding sequences which are followed by nosT transcription termination sequences.
Figure 5A:
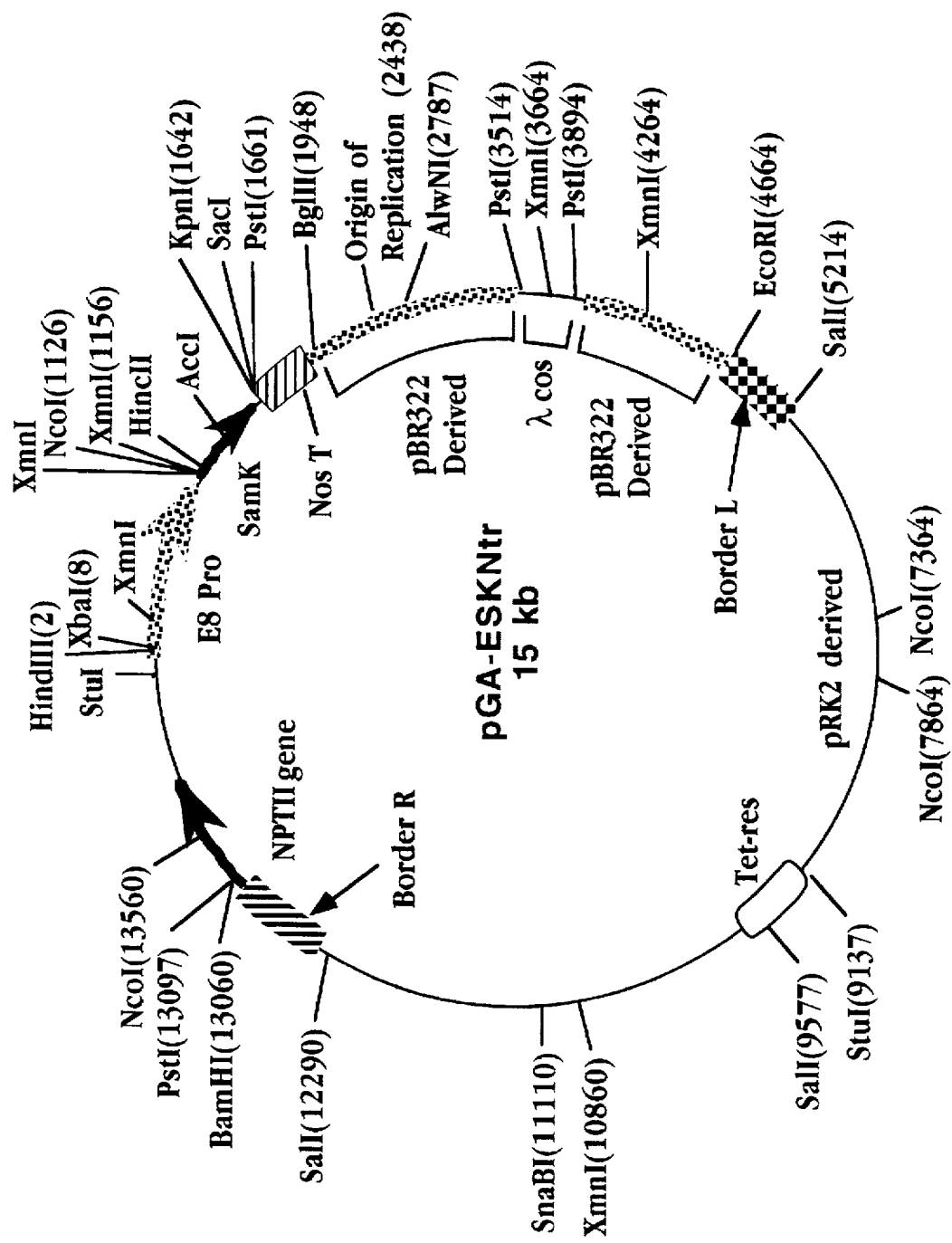
FIG. 5A schematically represents the structure of the pGA-ESKN vector.
Figure 5B:
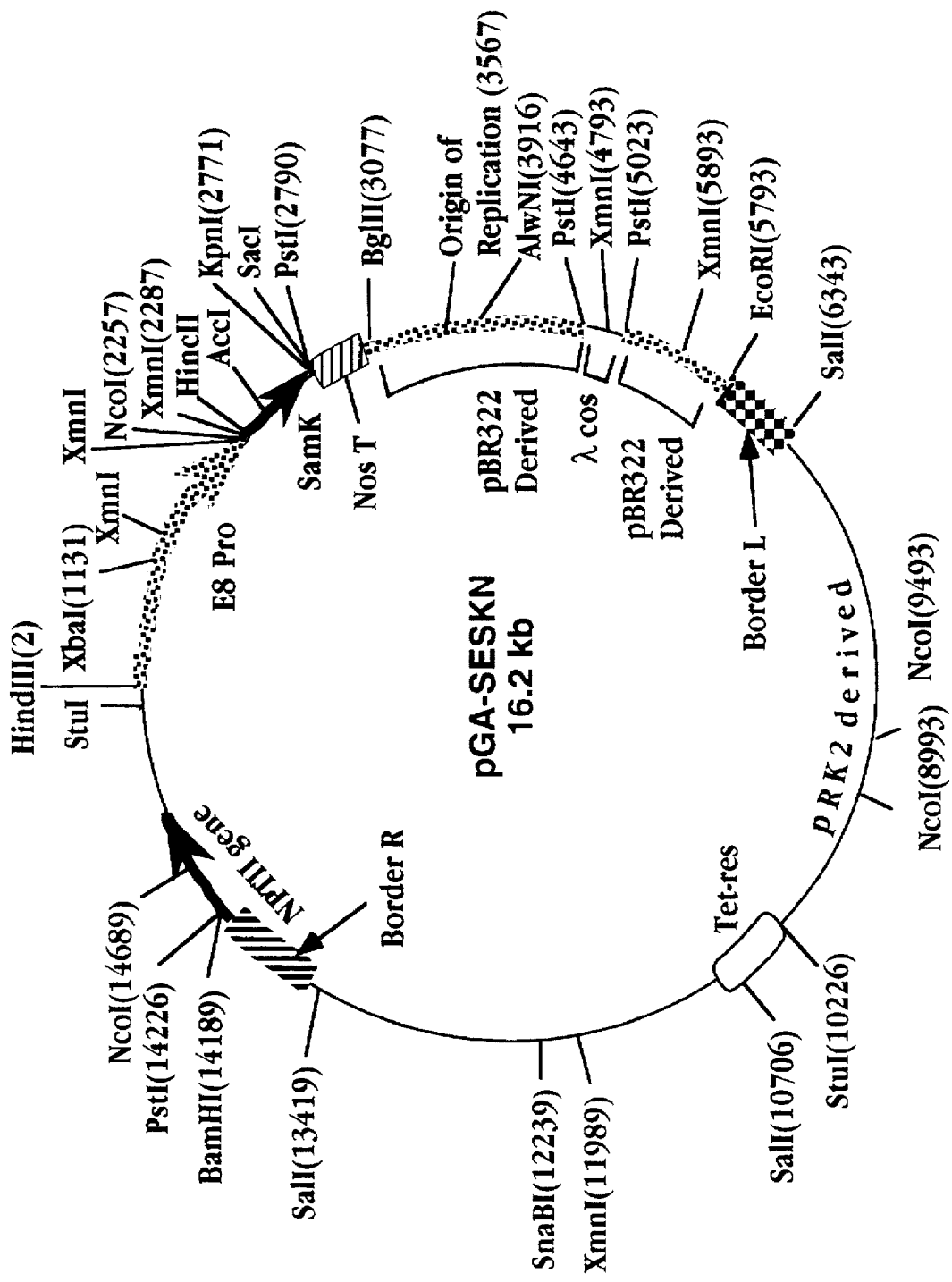
FIG. 5B schematically represents the structure of the pGA-SESKN vector.

Two AdoMetase expressing vectors were constructed (Example 1), the pGA-ESKN vector (FIGS. 12D and FIG. 5A) and the pGA-SESKN vector (FIG. 4 and FIG. 5B). The pGA-ESKN vector contains a portion of the E8 promoter (FIG. 4, lower E8 promoter) adjacent the AdoMetase coding sequences. A lambda EMBL-3 clone containing genomic tomato sequences that hybridize to the −1124 E8 region was isolated and used as the source for a region upstream of the −1124 E8 (lower E8) promoter. Restriction mapping analysis and subcloning allowed identification of an approximately 1200 bp HindIII to XbaI fragment as the region immediately upstream of the original −1124 bp E8 promoter (FIG. 4). This region was added to the pGA-ESKN construct to yield pGA-SESKN, which contained the approximately −2254 bp E8 promoter fused to the AdoMetase gene (FIG. 4, SE8).

Both of these vectors were transferred to tomato plants (Example 2) to generate transgenic plants expressing AdoMetase. A number of methods, in addition to Agrobacterium-based methods, may be employed to elicit transformation of the plant host, such as electroporation, microinjection, and microprojectile bombardment. These methods are well known in the art (Klein, et al.; Miki, et al.; Bellini, et al.). Further, these methods provide the means to introduce selected DNA into plant genomes: such DNA may include a DNA cassette which consisting of the E8 gene promoter functionally adjacent AdoMetase coding sequences.

Figure 6:
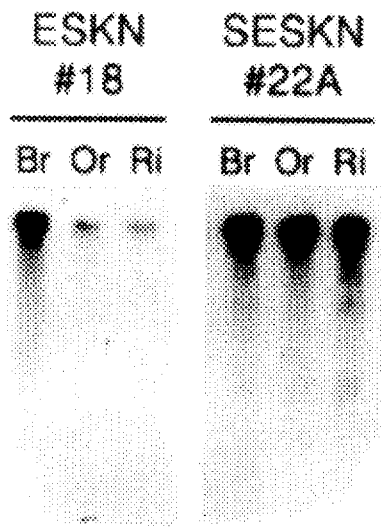
FIG. 6 shows the photograph of an autoradiogram which demonstrates the AdoMetase mRNA levels in fruit derived from two different transgenic plants.
Figure 7:
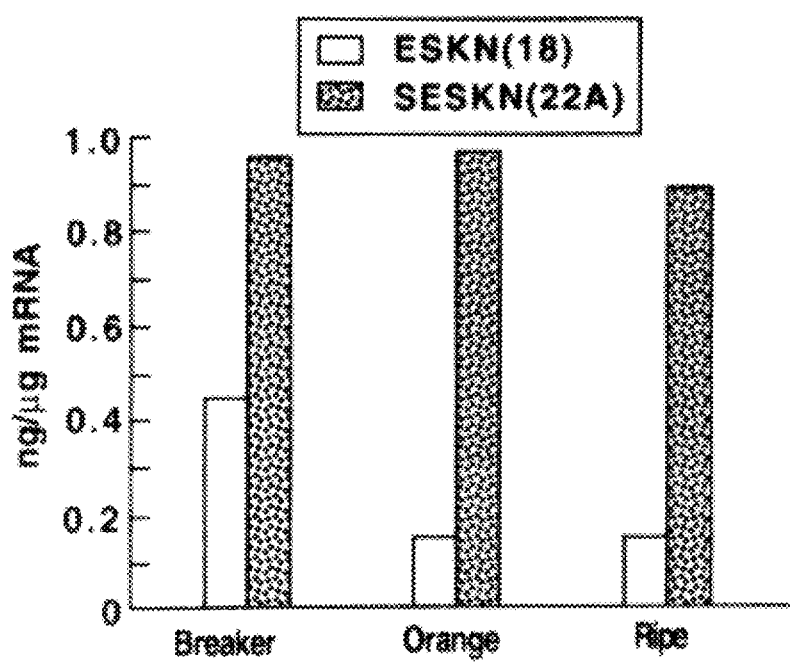
FIG. 7 shows a guantitation of the results presented in FIG. 6. These results illustrate the effect of variations of the E8 promoter on AdoMetase mRNA levels in ripening tomatoes.

Several transgenic plants were assayed for their ability to synthesize AdoMetase mRNA using a sensitive RNAase protection assay (RPA) (Example 3). FIGS. 6 and 7 show the results of an RPA using the fruit from two transgenic plants (ESKN and SESKN) at different stages of fruit ripening. Other tissues from these plants including immature and mature leaves, flowers and stems were negative for the presence of AdoMetase RNA. Although the expression of AdoMetase in ESKN transgenic plants was regulated to the post mature green fruit, it was repeatedly observed (as shown in FIGS. 6 and 7) that the expression of AdoMetase turned off in the fully ripe fruit. On the other hand, the SESKN transgenic fruit maintained AdoMetase mRNA expression in ripe fruit.

Figure 8:
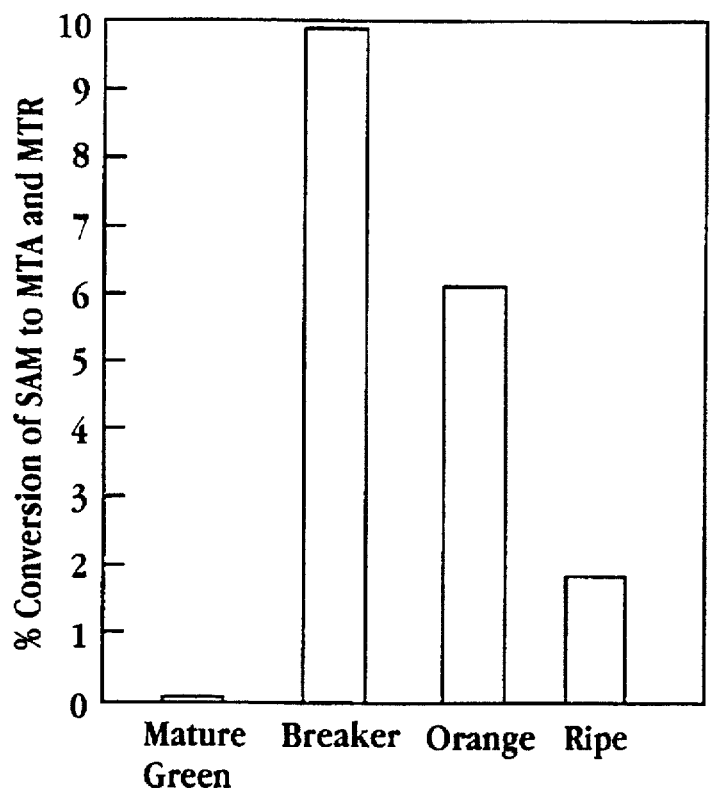
FIG. 8 is a graph representing the relative levels of AdoMetase activity in ripening tomatoes at different stages.

To determine whether the presence of AdoMetase enzyme activity correlated with the level of AdoMetase mRNA, an AdoMetase assay was performed using extracts from four fruit obtained at different stages from an ESKN transgenic plant (Example 5). FIG. 8 shows the level of AdoMetase activity in mature green, breaker, orange, and ripe fruit from a single pGA-ESKN transgenic plant. These data demonstrate that AdoMetase activity follows roughly the same expression pattern in ripening fruit as the AdoMetase-mRNA levels.

The data presented above suggest that inclusion of the upstream region of the native E8 promoter in the AdoMetase expression construct enhances long-lived AdoMetase gene expression in ripening transgenic tomatoes. FIG. 6 shows the RPA results from pGA-SESKN line 22A-1 and from pGA-ESKN line 18. ESKN line 18 had one of the highest levels of AdoMetase expression of all the ESKN transgenic lines. Quantitative measurement of AdoMetase mRNA is shown in FIG. 7. The results show that the −2254 bp E8 promoter expression is maintained through the fully ripe stage of fruit development. This expression pattern is in sharp contrast to the −1124 bp E8 promoter (ESKN) mRNA levels also shown in FIG. 6.

Ethylene evolution measurements from fruit picked at breaker and analyzed daily are shown in FIG. 9. The rate at which fruit from SESKN lines 22A and 35-1 produced lycopene was reduced as evidenced by the time required for orange fruit development. Furthermore, the total amount of ethylene produced from these tomatoes was reduced by approximately 80%. The expression of AdoMetase and a reduction in ethylene biosynthesis was strictly correlated in the 25 SESKN transgenic plants analyzed.

Figure 10:
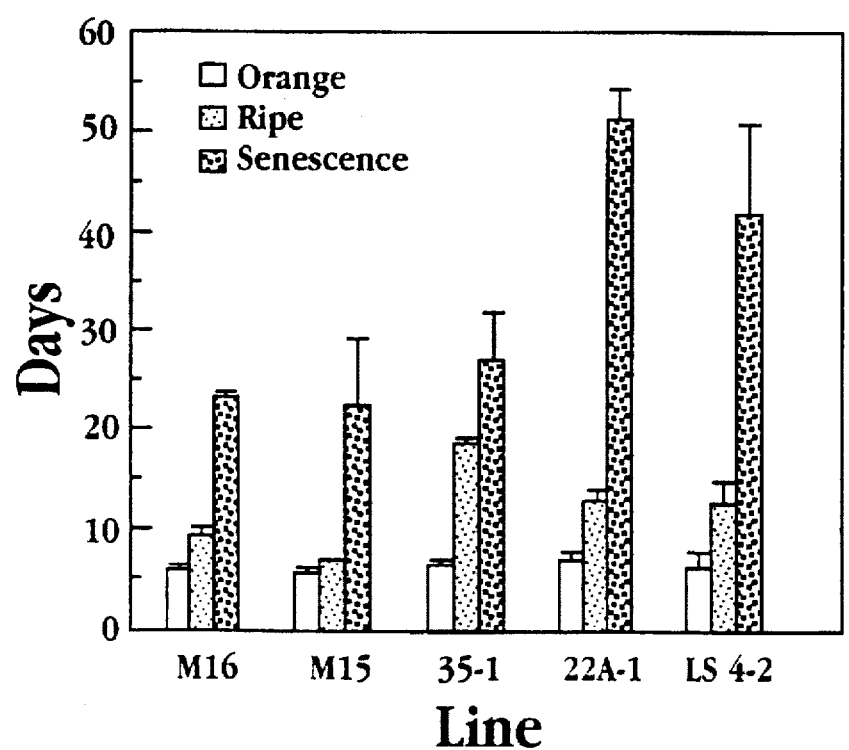
FIG. 10 illustrates the post-harvest shelf life of tomatoes obtained from SESKN transgenic plants.
Figure 9A:
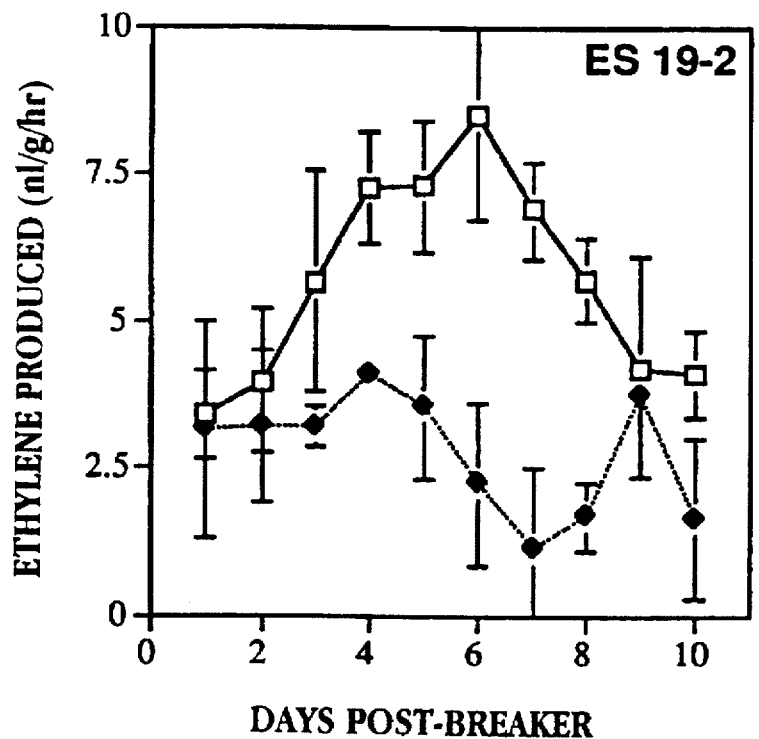
FIGS. 9A–9D present the data for ethylene production in the fruit of 4 different transgenic plants (FIG. 9A, ES 19-2 FIG. 9B, LS 4-2.
Figure 9B:
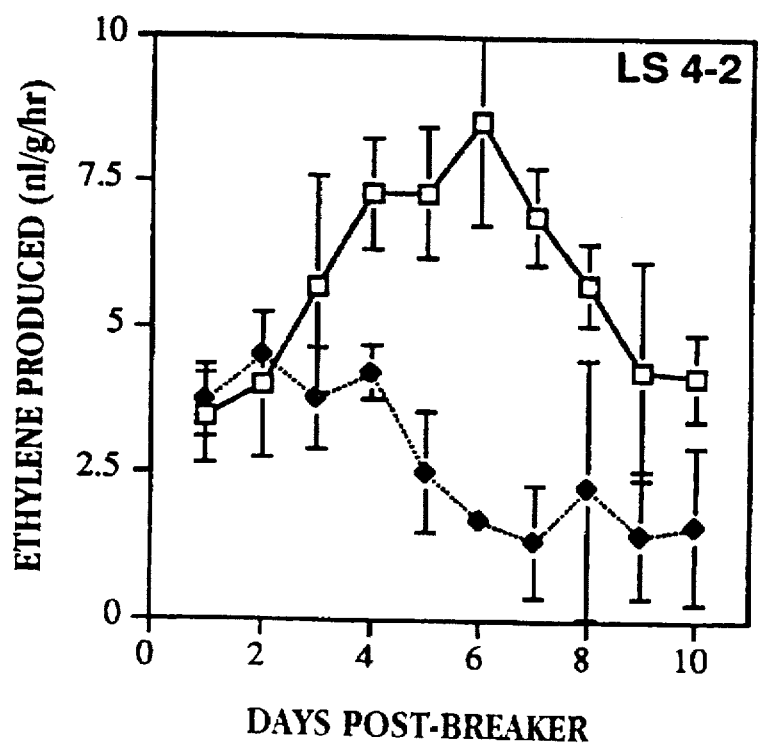
Figure 9C:
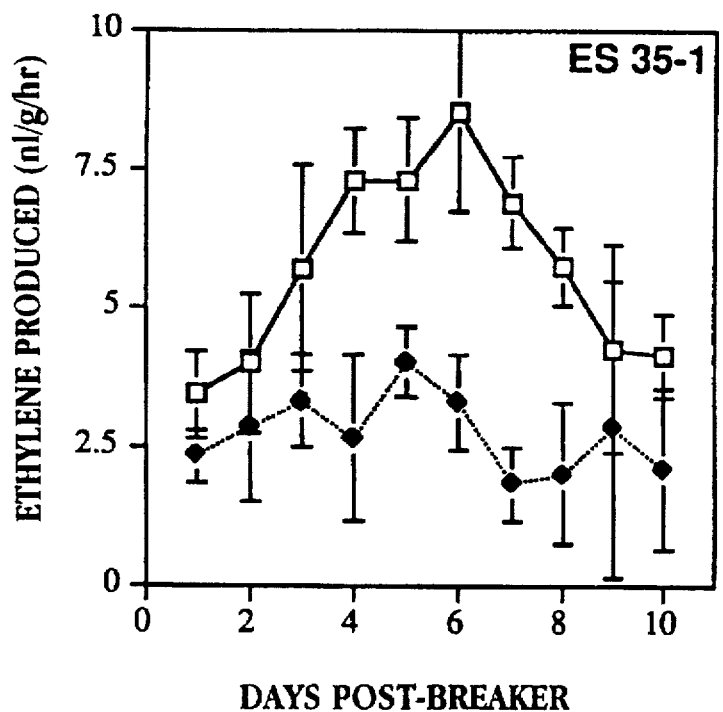
Figure 9D:
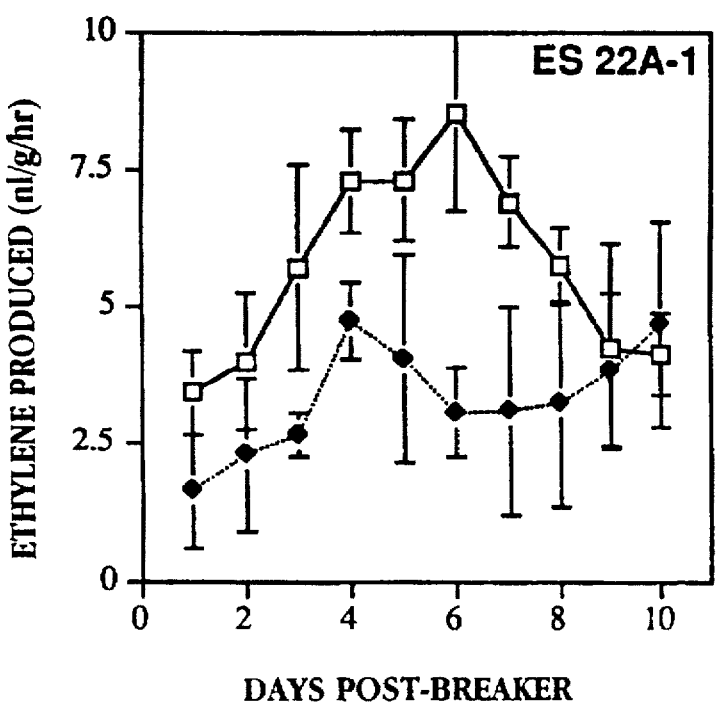

The SESKN tomatoes that synthesized less ethylene were assessed for their shelf life properties when stored at room temperature (22° C.) (Example 5). Three fruit each from SESKN lines 22A-1 and 35-1 were compared with untransformed normal tomatoes. Senescence was determined by visually observing contraction and wrinkles on the tomato skin. Firmness was not measured but was noted to be much greater in the transgenic lines. The results of these senescence assessments are shown in FIG. 10. Even at 55 days post-breaker, the 22A-1 tomatoes remained firm and appeared to be suffering more from dehydration than from the softening-induced senescence of the normal tomatoes.

These results demonstrate the ability to provide tissue specific regulation to the AdoMetase enzyme in transgenic plants. In addition, the results obtained with the two different E8 promoters (lower E8 and SE8) suggest the use of these promoters for similar tissue specific expression of any desired gene product. A tissue or stage specific promoter is a region of DNA that regulates transcription of the immediately adjacent (downstream) gene to a specific plant tissue or developmental stage of the plant or plant tissue. Other gene products which may be useful to express using these promoters include genes encoding (i) flavor or color modification proteins, and (ii) enzymes, such as is encoded by the taumatin gene, that modify lycopene synthesis. Further, it is useful to restrict expression of some genes to specific tissues, such as the fruit—for example, any gene that would be deleterious to the plant if it were expressed constitutively. Such genes would include genes which encoded degradative enzymes that deplete necessary metabolites. As can be seen from the results described above, derivatives of the E8 promoter region can be used as on/off switches for the tissue and stage specific expression of genes whose expression is under their control.

The present method is applicable to all higher plants. Regulatable promoters other than the E8 promoter can also be used in the practice of the present invention include, but are not limited to the following: the E4 gene promoter from tomatoes; and, the promoter for ethylene forming enzyme (EFE) from tomatoes. Further, the two regions of the E8 promoter (lower E8 and upper E8, FIG. 4) can be used as hybridization probes against libraries of DNA representative of the genomes of other plant species. Homologous sequences to the E8 promoter are then tested for tissue specific expression in the plant species from which they were isolated. Such promoters, as well as the E8 promoter itself, can be tested for regulatable expression in heterologous plant systems using the methods described herein. A reporter gene, such as GUS (β-glucuronidase), can be used to test tissue specific regulatable expression from these promoters. Expression of GUS protein can be easily measured by fluorometric, spectrophotometric or histochemical assays (Jefferson, 1987).

Variants of the E8 promoter may be isolated from different tomato cultivars by standard recombinant manipulations such as primer specific amplification (Mullis; Mullis, et al.) or oligonucleotide hybridization (Ausubel, et al.; Sambrook, et al.).

Another gene whose promoter may be used for AdoMetase expression is the polygalacturonase gene promoter from tomato.

The following examples illustrate, but in no way are intended to limit the present invention.

Materials and Methods

Tomato seed (*Lycopersicon esculentum* Mill. var. cerasiforme (Dunal) Alef. cv. Large Red Cherry) were obtained from Peto Seed, Inc. (Saticoy, Calif.) and were grown under standard greenhouse conditions. Harvested fruit were stored at room temperature (22° C.).

EXAMPLE 1

Cloning of the AdoMetase Gene

A. Isolation of the AdoMetase Gene.

The AdoMetase gene was identified on an AluI-HaeIII restriction fragment from purified T3 DNA (Hughes, et al., 1987a). Bacteriophage T3 is available under ATCC No. 11303-B3 (American Type Culture Collection, 12301 Parklawn Dr., Rockville Md. 20852). The DNA fragment was first cloned into the bacteriophage M13 MP8 vector (Pharmacia LKB Biotechnology, Inc., Pistcataway, N.J.). A MaeIII to BamHI fragment was subcloned into the pUC19 plasmid vector (Pharmacia) to produce pUC19-AdoMetase (pUC19-SAMase; FIG. 2). The generation of the pUC19-AdoMetase vector was described in parent application U.S. patent application Ser. No. 07/613,858, filed 12, Dec. 1990, herein incorporated by reference. This vector was transformed into *E. coli* and used as a source of DNA for further construction experiments and for DNA sequence determination.

B. Modification of the Amino-Terminal Sequence of the Cloned AdoMetase Gene.

The cloned AdoMetase gene was further engineered to contain a consensus eukaryotic translation initiation site (Kozak; Lutcke, et al.) by altering the nucleotide sequence surrounding the SAMase ATG start-codon using a synthetic double-stranded oligonucleotide.

The plasmid pUC19-AdoMetase was digested with XmaI and BamHI and the 1.9 kb and 1.3 kb fragments were purified by electro-elution after agarose gel electrophoresis. A double stranded synthetic oligonucleotide linker formed by annealing single-stranded oligonucleotides represented by SEQ ID:3 and SEQ ID NO:5 and having the sequence indicated in FIG. 2 was ligated to the 1.9 kb fragment and this ligated DNA subjected to XmaI digestion to remove excess linkers.

The linkered 1.9 kg fragment was then re-purified by electrophoresis on low melting temperature agarose and ligated to the 1.3 kb fragment to form the plasmid pUC19-SAM-K. The altered gene region was subjected to DNA sequence analysis. The gene sequence (SEQ ID NO:10)is given in FIGS. 11A–11D. This gene was designated SAM-K and used to construct the following plant expression vectors. This plasmid DNA lan also be used to directly transform the plant host via electroporation, microinjection, or microprojectile bombardment.

C. Vector Constructions using the Tomato E8 Promoter.

Two different forms of the E8 promoter were used to construct SAM-K-containing vectors. The first (−1124 bp) was isolated from tomato (*Lycopersicon esculentum* var. cerasiform) DNA using polymerase chain reaction (PCR) (Mullis; Mullis, et al.; Perkin-Elmer Cetus, Norwalk Conn.). The primers used in the PCR reaction were based on the sequence described by Deikman, et al. (1988). The sequences of the oligonucleotide primers (SEQ ID NO:8, SEQ ID NO:9) are given in FIG. 3. The oligonucleotides were designed to incorporate restriction endonuclease sites (XbaI and NcoI) at the 5' and 35' ends, respectively, of the amplified E8 -promoter fragment. These restriction endonuclease cleavage sites facilitated subcloning into the pUC19-SAM-K vector (see FIG. 2): an NcoI site is present near the ATG start codon region in the synthetic oligonucleotide.

Figure 12A:
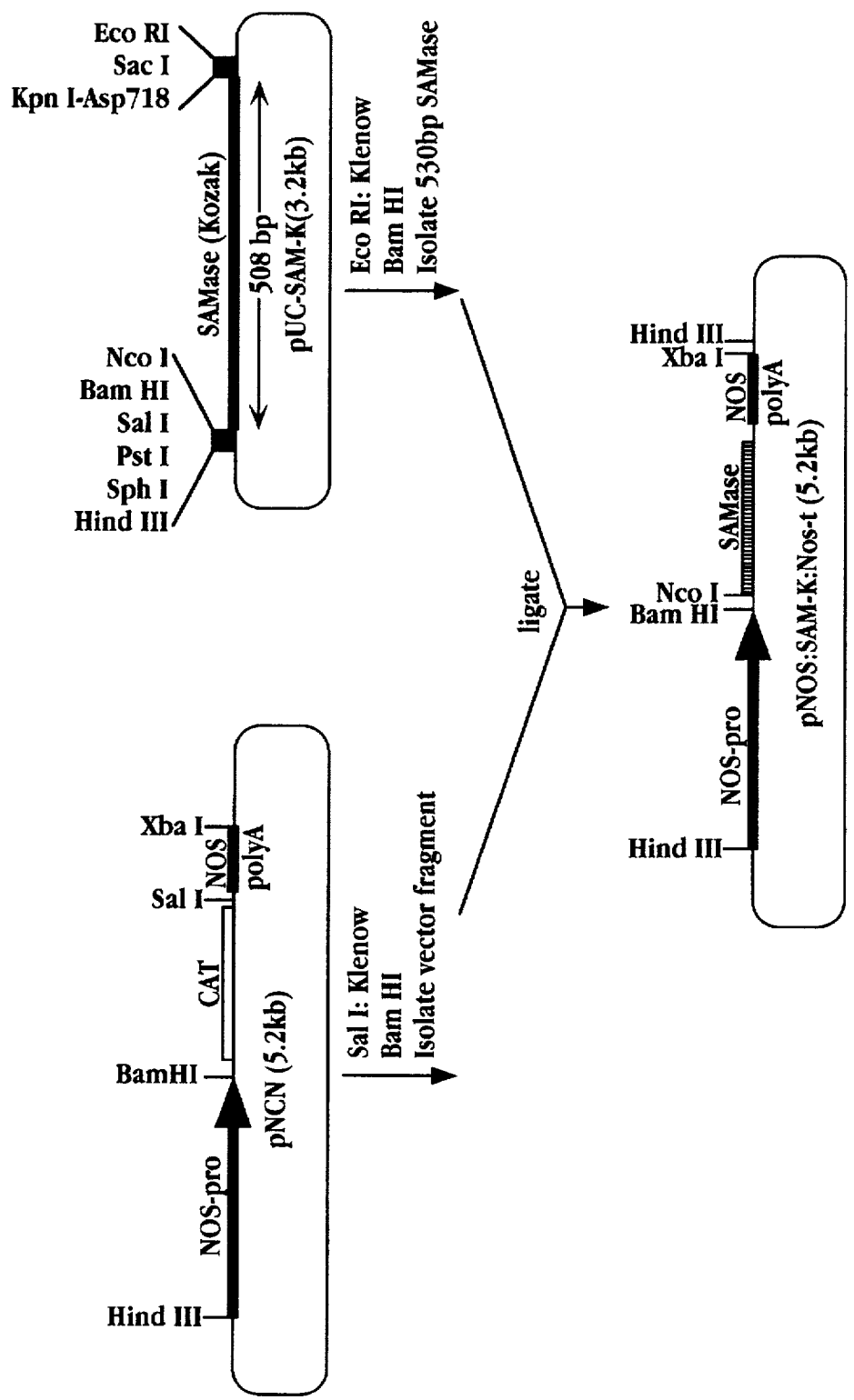
FIGS. 12A–12C outline the steps involved in the construction of the vector pESKN.
Figure 12B:
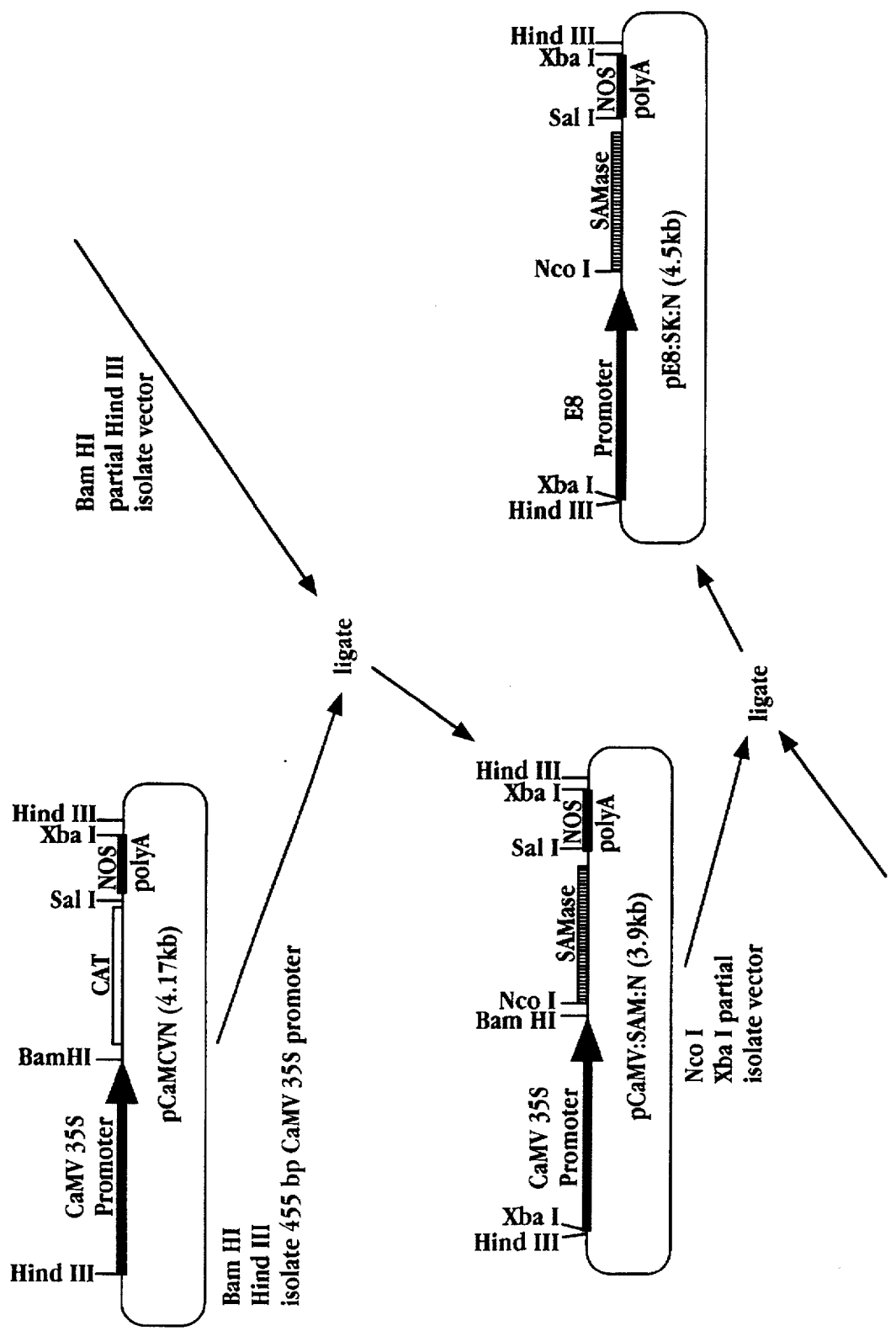
Figure 12C:
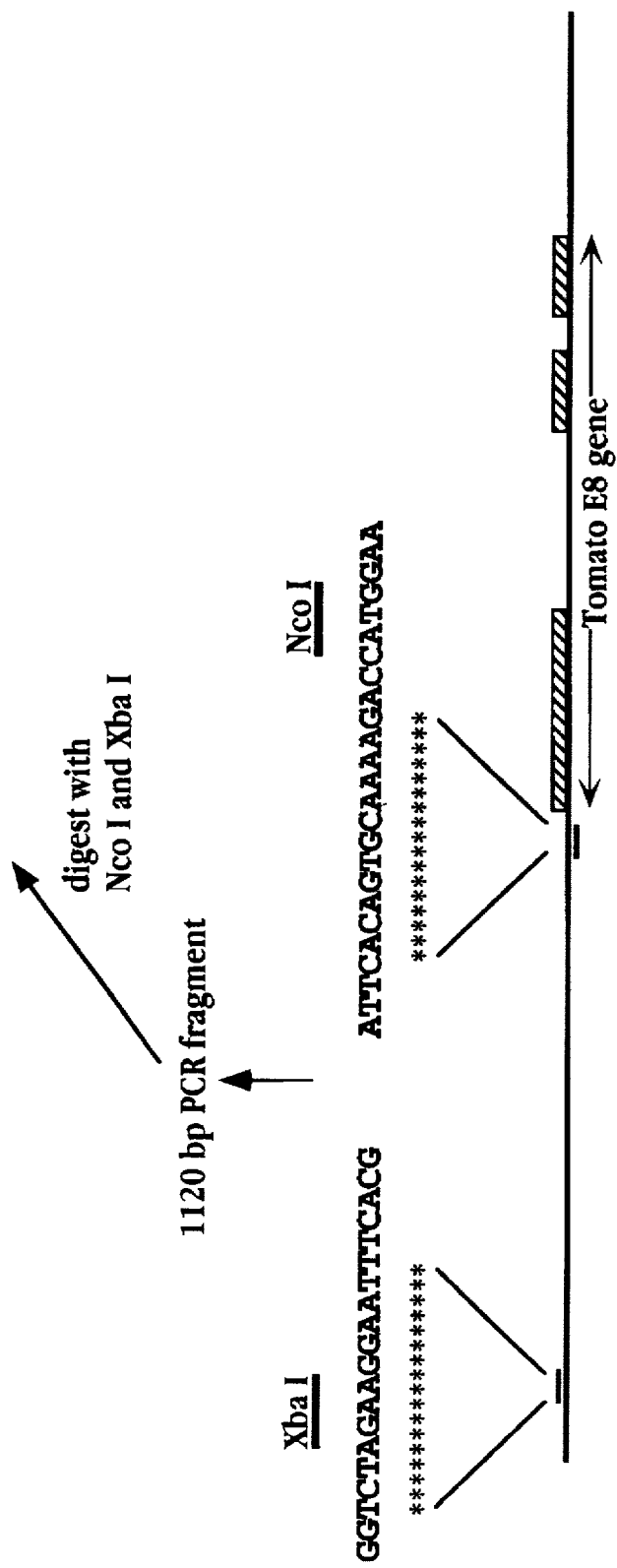

FIGS. 12A–12C outlines the generation of the vector pESKN starting from vector pNCN (Pharmacia, Inc., Piscataway, N.J.) and pUC-SAM-K (described above). The sequence of the E8 promoter (the lower E8 promoter) is similar to the sequence presented as bases 1090 to 2214 of SEQ ID NO:12, FIG. 13).

Figure 12D:
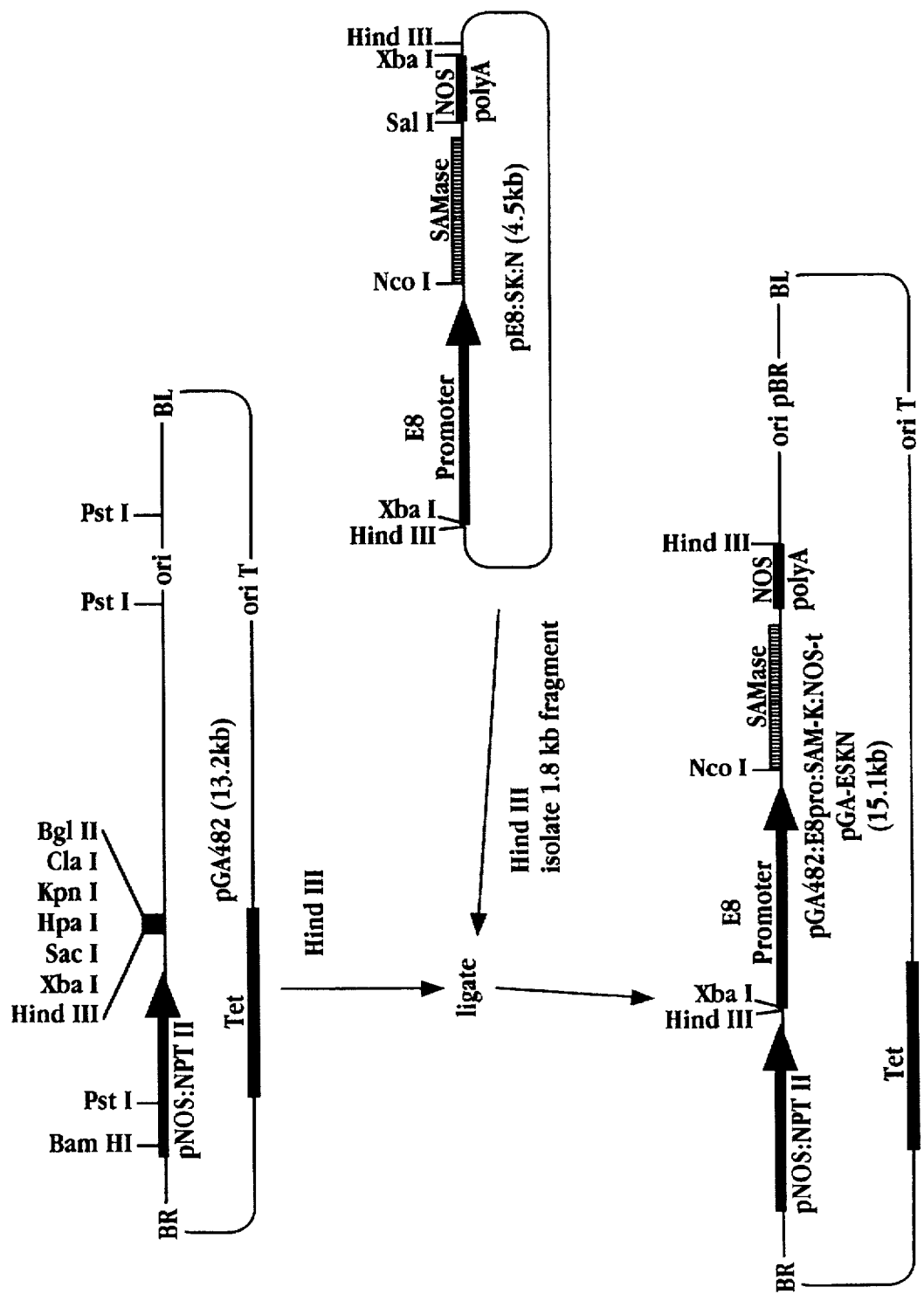
FIG. 12D outlines the steps involved in the modification of pESKN to the vector pGA-ESKN.

FIG. 12D outlines one approach to the generation of Agrobacterium vectors for use in the present invention. However, the E8 /AdoMetase cassette, present in, for example, pESKN, can be incorporated in a number of vectors useful for plant transformation.

Agrobacterium binary vectors were developed from pGA482 (An, et al., 1985), a pBIN19 derivative (Clontech Laboratories) containing the neomycin phosphotransferase II gene fused to the nopaline synthesis gene promoter (An, et al., 1988). The resulting vector, designated pGA-ESKN is shown in FIG. 5A.

The second E8 promoter (−2254 bp) was isolated from a lambda EMBL-3 clone that contained the entire E8 gene. The E8 gene clone was selected from a tomato. (*Lycopersicon esculentum* var. VFN8) genomic library obtained from Clontech Laboratories (Palo Alto, Calif.)

using the PCR-derived E8 promoter fragment (described above) as a hybridization probe in plaque-lift filter hybridizations. The lambda clone carrying the E8 gene was identified by a positive hybridization signal. The E8-bearing phage was plaque purified and the lambda phage DNA isolated.

The lambda E8 genomic clone was used as a source of the HindIII to XbaI fragment that is the approximately −2254 to −1124 bp upstream region of the E8 promoter. This fragment was inserted 5' of the approximately −1124 bp E8 promoter in pGA-ESKN at the HindIII and XbaI sites (FIG. 4). The resulting plasmid was named pGA-SESKN. FIGS. 13A and 13B show the nucleotide sequence (SEQ ID NO:12) of the −2216 bp region from one cultivar (Deikman, et al., 1988, 1992). The HindIII to XbaI fragment (used for construction of the approximately −2254 promoter) contains additional sequences 5' to the end of this −2216 bp sequence.

FIG. 4 shows the relationship of the two portions of the E8 promoter that are present in pGA-SESKN.

Standard recombinant DNA techniques were employed in all constructions (Adams, et al.; Ausubel, et al.). Another lambda vector, pGEM7Zf(+)SAM-K, was constructed by cloning the BamHI to KpnI AdoMetase fragment from pUC19:SAM-K into the same sites of pGEM7Xf(+) (Promega, Inc., Madison, Wis).

Other plant cloning vectors, such as pBI121 (Clontech Laboratories, Inc., Palo Alto, Calif.), can also be used to practice the present invention. The plant promoter upstream of the AdoMetase gene sequence can be varied to obtain tissue specific expression, temperature dependent expression, or light dependent expression in the transgenic plants. Another useful plant promoter, in addition to the E8 promoter described above, is the constitutive Cauliflower Mosaic Virus (CaMV) promoter (Pharmacia).

EXAMPLE 2

Plant Transformation

The pGA-SESKN and pGA-SESKN AdoMetase plasmids were separately introduced into Agrobacterium using a direct transformation method.

*Agrobacterium tumefaciens* strain EHA101 (Hood, et al.), a disarmed derivative of *Agrobacterium tumefaciens* strain C58, was used to introduce coding sequences into plants. This strain contains a T-DNA-less Ti plasmid. The pGA-ESKN and pGA-SESKN AdoMetase plasmids were transferred into EHA101 using electroporation essentially as described by Nagel, et al. Briefly, an *Agrobacterium tumefaciens* culture was grown to mid-log phase (OD 600 0.5 to 1.0) in YEP media (10 g yeast extract, 10 g peptone, and 5 g NaCl per liter). After chilling on ice, 50 mls of these cells were pelleted, resuspended in 1 ml of ice cold 20 mM $CaCl_2$ and split into 1 ml aliquots.

Typically, one μg of plasmid DNA was added to an aliquots and incubated on ice for 30 minutes. The aliquot was then frozen in liquid nitrogen and thawed at 37° C. for 5 minutes. One ml of YEP media was added and incubated at 28° C. for 2 hours. The cells were pelleted, resuspended in 50 μl of YEP, and plated on YEP agar plates containing 20 μg/ml kanamycin. Kanamycin-resistant transformed colonies appear within 2 days.

Tomato cotyledon tissue explants were excised from both the tip and base of the cotyledon. Cotyledon explants were pre-conditioned for 2 days on tobacco feeder plates (Fillatti, et al.). The pre-conditioned explants were inoculated with EHA101 containing the pGA-ESKN or pGA-SESKN AdoMetase plasmid of interest and finally placed in a 10 ml overnight culture of EHA101 for 5 minutes. The explants were then co-cultivated with the EHA101 strains for 2 days on tobacco feeder plates as described by Fillatti, et al.

The explants were grown in tissue culture media (Fillatti, et al.) containing 2Z media, MS salts, Nitsch and Nitsch vitamins, 3% sucrose, 2 mg/l seatin, 500 mg/l carbenicillin, 100 mg/l kanamycin and 0.7% agar. The explants were grown in tissue culture for 8 to 10 weeks. The carbenicillin treatments were kept in place for 2 to 3 months in all media. The explants and plants were kept on carbenicillin until they were potted in soil as a counter-selection to rid the plants of viable *Agrobacterium tumefaciens* cells.

EXAMPLE 3

RNAase Protection Assays for the Detection of SAMase mRNA

Tomato fruits at various stages of development from transgenic plants and wild-type plants were used as mRNA sources. mRNA was extracted from tomato cells and purified using the "QUICK PREP RNA" kit from Pharmacia, Inc. RNAse Protection Assays (RPA) were performed following the manufacturer's instructions using an "RPAII" kit from Ambion, Inc. (Hialeah, Fla.). This method has been previously described by Lee, et al.

pGEM7Zf(+)SAM-K was used to generate $^{32}$P-UTP-labeled RNA probe using bacteriophage T7 RNA polymerase as contained in the "RIBOPROBE IT T7 RNA POLYMERASE SYSTEM" from Promega, Inc. The radiolabeled probe was purified on a preparative polyacrylamide gel and used for up to one week.

One microgram of isolated mRNA was hybridized to approximately 10,000 CPM of the RNA probe and further processed as per the instructions in the "RPA II" kit. Briefly, one microgram of the purified mRNA was mixed with 10,000 CPM of the RNA probe in a total volume of 15 μl. 20 μl of a hybridization buffer that allows hybridization of complementary sequences (Ausubel, et al.; Maniatis, et al.; Sambrook, et al.) is then added. The hybridization solution is provided in the "RPAII" kit from Ambion. The solution was heated to 90° C. for 3–4 minutes to denature all the RNA and incubated at 45° C. overnight to allow hybridization of complementary sequences. The solution was cooled to 37° C. and RNase (provided in the Ambion kit) was added which degrades all unhybridized probe.

Protected probe was resolved on a denaturing polyacrylamide gel, dried, and exposed to film for up to 16 hours. Quantitative analysis of the RPA signals was accomplished by excising each band from the gel, dissolving the band in a liquid fluor, and determining the radioactivity present in the sample using liquid scintillation counting A standard curve was generated using various amounts of unlabeled RNA synthesized from a AdoMetase fragment cloned into pGEM5Z(+) in the sense orientation. The linear range of the assay was dependent on the amount of input $^{32}$P-labeled RNA probe in the RNAase protection assay but typically ranged from 10 pg to 1 ng of mRNA.

EXAMPLE 4

Ethylene Measurements

The assay for tomato ethylene evolution is performed over a 0.5 to 1.0 hour period by sealing glass jars containing individual fruit and sampling 2 ml aliquots for gas chromatographic analysis. A Hewlett Packard 5890 (Palo Alto, Calif.) gas chromatograph with a flame ionization detector and a 6 ft Porapak N column was used for ethylene measurements (Adams, et al.). This system combined with an HP Vectra computer and the current version of "CHEMSTATION" (Hewlett Packard) allows measurement of ethylene concentrations as low as 0.2 nl of ethylene in a 2 ml sample (0.1 ppm). After measurement of the ethylene in the headspace, the values are converted to nl of ethylene per gram of tissue per hour.

EXAMPLE 5

Characterization of Transgenic Tomatoes

A. Promoter Effect on SAMase mRNA Levels in Ripening Transgenic Fruit.

Transgenic fruit were selected from two transgenic plants, ESKN #18 and SESKN #22A, at three stages of ripening, breaker (Br), Orange (Or) and Ripe (Ri). Transgenic plant ESKN #18 contained the lower E8 promoter (FIG. 4) adjacent the Sam-K AdoMetase gene. Transgenic plant SESKN #22A contained the entire SE8 promoter (FIG. 4) adjacent the Sam-K AdoMetase gene. The AdoMetase mRNA level in ripening transgenic fruit was determined as described in Example 3.

The products of the RNA protection assay were resolved on polyacrylamide gels and exposed to X-ray film. A representative autoradiogram of the RNA protection assay is presented in FIG. 6. As can be seen in the figure, AdoMetase mRNA was present in both transgenic plants at the breaker stage of fruit ripening However, the levels of AdoMetase mRNA drop in the ESKN transgenic plant, relative to the SESKN transgenic plant, at the orange and ripe stages of fruit ripening The level of AdoMetase-mRNA was quantitated as described in Example 3 by liquid scintillation counting and determination of mRNA concentrations relative to a standard curve. FIG. 7 presents the results of this analysis. The results are consistent with those shown in FIG. 6. AdoMetase mRNA was present in both transgenic plants at the breaker stage of fruit ripening with the concentrations lower in ESKN #18. At the orange and ripe stages of fruit ripening the levels of AdoMetase-mRNA drop in the ESKN transgenic plant, relative to the level at breaker stage and the levels in the fruit from the SESKN transgenic plant. The AdoMetase mRNA levels stay relatively constant in the SESKN transgenic plant.

B. Relative Levels of SAMase Activity in Ripening Transgenic Tomatoes.

To determine whether the presence of AdoMetase enzyme activity correlated with the level of AdoMetase mRNA, a 14C-SAM-based AdoMetase assay was performed using extracts from four different fruit stages from a single pGA-ESKN transgenic plant.

Plant tissues to be assayed for AdoMetase enzyme activity were frozen and ground to a powder in liquid nitrogen. The ground tissue was then suspended in 1.5 volumes of 200 mM Tris-HCl (pH 7.5), 10 mM DTT, and 10 mM EDTA. The suspension was vortexed vigorously then subjected to centrifugation at 40,000×g at 4° C. for 20 minutes. The following was added to 50 µl of extract: 5 µl of $^{14}$C-SAM (DuPont-New England Nuclear, NEC-363) a µCi/ml and a specific activity of 58.0 mCi/mmol. The reaction was incubated at 37° C. for 1 hour then 40 µl of the reaction was spotted on a cellulose think layer chromatography (TLC) plate (J. T. Baker, Inc., Phillipsburg, N.J., Baker-Flex Cellulose F) and resolved for 3 hours in 70:70:20:40, butanol:acetone:acetic acid:water. The MTA and MTR spots were identified using autoradiography, excised, and counted using liquid scintillation.

FIG. 8 shows the level of AdoMetase activity in mature green, breaker, orange, and ripe fruit. The level of AdoMetase activity is defined as the percent conversion of SAM (S-adenosylmethionine) to MTA (5'-Methylthioadenosine) and MTR (5'-Methylthioribose). The decreasing level of AdoMetase activity from breaker to ripe fruit in the ESKN transgenic plant is consistent with the AdoMetase-mRNA levels shown in FIG. 7.

Untransformed tomato fruit extracts do not degrade SAM to MTA or MTR at any stage of ripening when used in this assay.

C. Ethylene Production in Ripening Transgenic Fruit.

Ethylene produced from transgenic tomatoes carrying the AdoMetase gene under the regulation of the SE8 promoter (FIG. 4) was determined as described in Example 4. Greenhouse grown tomatoes from 4 transgenic lines were tested. The results of the analysis are presented in FIGS. 9A to 9D. Each of the four graphs shown in FIG. 9 represent the comparison of fruit from one pGA-SESKN transgenic line (Es 19-2, LS 4-2, ES 35-1 and ES 22A-1) with the fruit from untransformed controls. The control values (open squares) are the same in each of the four graphs and represent the average of six fruit from two different plants. The values from each transgenic line (closed symbols) are the average of ethylene determinations for three fruit. Error bars represent one standard deviation of the data.

The data represent a time period of ten days after the breaker stage of fruit ripening (post-breaker). These data demonstrate a reduction in the amount of ethylene production in transgenic tomatoes versus normal fruit over the ten day period.

D. Post-Harvest Shelf-life of SESKN Tomatoes.

Tomatoes from the SESKN transgenic plants that synthesized less ethylene were assessed for their shelf life properties when stored at 22° C. Three fruit from each from SESKN lines 35-1, 22A-1 and LS4-2 were compared with tomatoes from two untransformed, normal plants (M16 and M15). Senescence was determined each day by visual examination of the fruit for the occurrence of contraction and wrinkles on the tomato skin. The results of these senescence assessments are shown in FIG. 10.

As can be seen from the results in the figure, the bar graph shows the time for the fruit to achieve each stage: all fruit were picked at the breaker stage. For instance, line 35-1 took 18 days to ripen (Ripe stage) but then senescence developed at day 27. Line 22A-1 took 7 days to turn orange, 13 days to turn red, then 52 days to senescence. Even at 55 days post-breaker, the 22A-1 tomatoes remained firm and appeared to be suffering more from dehydration than from the softening-induced senescence of the normal tomatoes.

Firmness was not measured for the tomatoes from the five plants described above, however, the firmness was noted to be much greater in the fruit from the transgenic lines.

While the invention has been described with reference to specific methods and embodiments, it will be appreciated that various modifications and changes may be made without departing from the invention.

It is claimed:

1. A transgenic fruit-bearing plant, comprising: (i) a DNA sequence which encodes S-adenosylmethionine hydrolase enzyme, and (ii) a promoter capable of regulating expression of the tomato E8 gene, where expression redulated by said promoter is induced during fruit ripening or by ethylene synthesis by fruit of said plant, and where said DNA sequence is operably linked to said promoter to enable expression of S-adenosylmethionine hydrolase enzyme.

2. The transgenic plant of claim 1, wherein the promoter is from a tomato E8 gene.

3. Transgenic tomato fruit cells, comprising;
  (i) a DNA sequence which encodes S-adenosylmethionine hydrolase enzyme, and (ii) a promoter capable of regulating expression of the tomato E8 gene, where expression regulated by said promoter is induced during fruit ripening or by ethylene synthesis by said fruit, and where said DNA sequence is operably linked to said promoter to enable expression of S-adenosylmethionine hydrolase enzyme.

4. The transgenic tomato fruit cells of claim 3, wherein the promoter is from a tomato E8 gene.

5. The transgenic plant of claim 1, wherein said transgenic plant is a tomato plant.

6. The transgenic plant of claim 2, where the E8 promoter contains the sequence presented in FIGS. 13A and 13B.

7. The transgenic plant of claim 6, where the E8 promoter consists of bases 1090 to 2214 FIGS. 13A and 13B.

8. The transgenic plant of claim 1, wherein said enzyme coding sequence is derived from a bacteriophage selected from the group consisting of *Escherichia coli* bacteriophage T3, coliphage BA14, Klebsiella phage K11, and Seratti phage IV.

9. The transgenic plant of claim 8, where said enzyme coding sequence is derived from *Escherichia coli* bacteriophage T3.

10. The transgenictomato fruit cells of claim 4, where the E8 promoter contains the sequence presented in FIGS. 13A and 13B.

11. The transgenic tomato fruit cells of claim 10, where the E8 promoter consists of bases 1090 to 2214 in FIGS. 13A and 13B.

12. A method for reducing ethylene biosynthesis in fruit cells of a plant, comprising:
  providing a vector containing (a) a first DNA sequence containing a gene encoding a selectable marker functional in plant cells, where said first DNA sequence is flanked by regulatory elements effective to allow expression of the sequence in plant host cells, and (b) (i) a second DNA sequence which encodes S-adenosylmethionine hydrolase enzyme, and (ii) a promoter capable of regulating expression of the tomato E8 gene, where expression regulated by said promoter is induced during fruit ripening by ethylene synthesis by said fruit, and where said second DNA sequence is operably linked to said promoter to enable expression of S-adenosylmethionine hydrolase enzyme,
  transforming plant host cells with said vector, and
  growing the transformed host cells to produce a transgenic plant bearing fruit, wherein plant fruit cells are capable of expressing S-adenosylmethionine hydrolase enzyme.

13. The method of claim 12, where said second DNA sequence encodes the protein sequence presented in FIGS. 11A–11D.

14. The method of claim 12, where said enzyme coding sequence is derived from a bacteriophage selected from the group consisting of *Escherichia coli* bacteriophage T3, coliphage BA14, Klebsiella phage K11, and Seratti phage IV.

15. The method of claim 14, where said enzyme coding sequence is derived from *Escherichia coli* bacteriophage T3.

16. The method of claim 12, wherein said transforming of a plant host is carried out by an Agrobacterium-mediated transformation methodology.

17. The method of claim 12, wherein said transforming of a plant host is carried out by a direct transformation methodology selected from the group consisting of electroporation, microinjection, and microprojectile bombardment.

18. The method of claim 12, wherein said selectable marker confers kanamycin resistance.

19. The method of claim 12, where said promoter is a tomato E8 promoter.

20. The method of claim 19, where the E8 promoter contains the sequence presented in FIGS. 13A and 13B.

21. The method of claim 20, where the E8 promoter consists of 1090 to 2214 in FIGS. 13A and 13B.

22. A vector useful for transformation of a plant host, where said plant produces a fruit, comprising:
  (a) a first DNA sequence encoding a selectable marker functional in plant cells, where said first DNA sequence is flanked by regulatory elements effective to allow expression of the sequence in a plant host, and
  (b) (i) a second DNA sequence which encodes S-adenosylmethionine hydrolase enzyme, and (ii) a promoter capable of regulated expression of the tomato E8 gene, where expression redulated by said promoter is induced during fruit ripening or by ethylene synthesis by said fruit, and where said second DNA sequence is operably linked to said promoter to enable expression of S-adenosylmethionine hydrolase enzyme.

23. The vector of claim 22, where said plant host is a tomato.

24. The vector of claim 22, where said promoter is a tomato E8 promoter.

25. The vector of claim 24, where the E8 promoter contains the sequence presented in FIGS. 13A and 13B.

26. The vector of claim 25, where the E8 prometer consists of bases 1090 to 2214 in FIGS. 13A and 13B.

27. A duplex DNA fragment, comprising:
(i) a DNA sequence which encodes S-adenosylmethionine hydrolase enzyme, and adjacent said DNA sequence (ii) a promoter capable of regulating expression of the tomato E8 gene, where expression regulated by said promoter is induced during fruit ripening or by ethylene synthesis by a fruit, and where said DNA sequence is operably linked to said promoter to enable expression of S-adenosylmethionine hydrolase enzyme.

28. A method for modifying ripening fruit of a fruit bearing plant, comprising, growing the plant of claim 1 to produce a transgenic plant bearing fruit, wherein fruit produced by said plant has reduced ethylene biosynthesis relative to fruit produced by a nontransformed normal plant.

29. A method of extending the post-harvest shelf life of a fruit, comprising, growing the plant of claim 1, to produce a transgenic plant bearing fruit, wherein fruit produced by said plant has reduced ethylene biosynthesis relative to fruit produced by a nontransformed normal plant.

30. A fruit produced by the transgenic plant of claim 1.

31. A transgenic plant cell of a plant of claim 1.

32. A transgenic plant cell of a plant of claim 2.

33. The DNA fragment of claim 27, wherein the promoter is from a tomato E8 gene.

34. The DNA fragment of claim 33, where the E8 promoter contains the sequence presented in FIGS. 13A and 13B.

35. The DNA fragment of claim 34, where the E8 promoter consists of bases 1090 to 2214 in FIGS. 13A and 13B.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 81 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
( C ) INDIVIDUAL ISOLATE: Fig. 2, first DNA sequence ( i x ) FEATURE:
( A ) NAME/KEY: CDS
( B ) LOCATION: 49..81

( x i ) SEQUENCE DESCRIPTION: SEQ ID NO:1:

```
AAGCTTGCAT  GCCTGCAGGT  CGACTCTAGA  GGATCCCCGT  AACACCAA ATG ATT TTC      57
                                                         Met Ile Phe
                                                           1

ACT AAA GAG CCT GCG AAC GTC TTC                                            81
Thr Lys Glu Pro Ala Asn Val Phe
     5                    10
```

( 2 ) INFORMATION FOR SEQ ID NO:2:

( i ) SEQUENCE CHARACTERISTICS:
( A ) LENGTH: 11 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Ile Phe Thr Lys Glu Pro Ala Asn Val Phe
 1               5                    10
```

( 2 ) INFORMATION FOR SEQ ID NO:3:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Fig. 2, first synthetic
oligonucleotide ( i x ) FEATURE:
( A ) NAME/KEY: CDS
( B ) LOCATION: 12..38

( x i ) SEQUENCE DESCRIPTION: SEQ ID NO:3:

```
GATCCGCCAC C ATG GTT TTC ACT AAA GAG CCT GCG AAC G                         39
```

```
        Met  Val  Phe  Thr  Lys  Glu  Pro  Ala  Asn
         1                  5
```

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Val  Phe  Thr  Lys  Glu  Pro  Ala  Asn
 1                  5
```

( 2 ) INFORMATION FOR SEQ ID NO:5:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Fig. 2, second synthetic oligonucleotide sequence ( x i ) SEQUENCE DESCRIPTION: SEQ ID NO:5:

```
CGTTCGCAGG  CTCTTTAGTG  AAAACCATGG  TGGCG                                    35
```

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Fig. 2, T3 SAMase ( x i ) SEQUENCE DESCRIPTION: SEQ ID NO:6:

```
CACCAAATGA  TT                                                                12
```

( 2 ) INFORMATION FOR SEQ ID NO:7:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Fig. 2, SAM- K ( x i ) SEQUENCE DESCRIPTION: SEQ ID NO:7:

GCCACCATGG TT                                                                                              12

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Fig. 3, E8 5'primer ( x i ) SEQUENCE DESCRIPTION: SEQ ID NO:8:

GGTCTAGAAG GAATTTCACG                                                                                      20

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Fig. 3, E8 3'primer ( x i ) SEQUENCE DESCRIPTION: SEQ ID NO:9:

ATTCACAGTG CAAAAGACCA TGGAA                                                                                25

( 2 ) INFORMATION FOR SEQ ID NO:10:

( i ) SEQUENCE CHARACTERISTICS:
        ( A ) LENGTH: 586 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: Fig. 11, pUC19-SAM-K ( i x ) FEATURE:
        ( A ) NAME/KEY: CDS
        ( B ) LOCATION: 66..521

( x i ) SEQUENCE DESCRIPTION: SEQ ID NO:10:

```
ACAGCTATGA CCATGATTAC GCCAAGCTTG CATGCCTGCA GGTCGACTCT AGAGGATCCG         60

CCACC ATG GTT TTC ACT AAA GAG CCT GCG AAC GTC TTC TAT GTA CTG            107
      Met Val Phe Thr Lys Glu Pro Ala Asn Val Phe Tyr Val Leu
      1               5                   10

GTT TCC GCT TTC CGT TCT AAC CTC TGC GAT GAG GTG AAT ATG AGC AGA         155
```

|   |   |   |   |   |   |   |   |   |   |   |   |   |   |   |   |   |
|---|---|---|---|---|---|---|---|---|---|---|---|---|---|---|---|---|
| Val | Ser | Ala | Phe | Arg | Ser | Asn | Leu | Cys | Asp | Glu | Val | Asn | Met | Ser | Arg |   |
| 15 |  |  |  |  | 20 |  |  |  | 25 |  |  |  |  |  | 30 |   |
| CAC | CGC | CAC | ATG | GTA | AGC | ACT | TTA | CGT | GCC | GCA | CCG | GGT | CTT | TAT | GGC | 203 |
| His | Arg | His | Met | Val | Ser | Thr | Leu | Arg | Ala | Ala | Pro | Gly | Leu | Tyr | Gly |   |
|  |  |  |  | 35 |  |  |  |  | 40 |  |  |  |  | 45 |  |   |
| TCC | GTT | GAG | TCA | ACC | GAT | TTG | ACC | GGG | TGC | TAT | CGT | GAG | GCA | ATC | TCA | 251 |
| Ser | Val | Glu | Ser | Thr | Asp | Leu | Thr | Gly | Cys | Tyr | Arg | Glu | Ala | Ile | Ser |   |
|  |  |  | 50 |  |  |  |  | 55 |  |  |  |  | 60 |  |  |   |
| AGC | GCA | CCA | ACT | GAG | GAA | AAA | ACT | GTT | CGT | GTA | CGC | TAC | AAG | GAC | AAA | 299 |
| Ser | Ala | Pro | Thr | Glu | Glu | Lys | Thr | Val | Arg | Val | Arg | Tyr | Lys | Asp | Lys |   |
|  |  | 65 |  |  |  |  | 70 |  |  |  |  | 75 |  |  |  |   |
| GCG | CAG | GCA | CTC | AAT | GTT | GCA | CGC | CTA | GCT | TGT | AAT | GAG | TGG | GAG | CAA | 347 |
| Ala | Gln | Ala | Leu | Asn | Val | Ala | Arg | Leu | Ala | Cys | Asn | Glu | Trp | Glu | Gln |   |
|  | 80 |  |  |  |  | 85 |  |  |  |  | 90 |  |  |  |  |   |
| GAT | TGC | GTA | CTG | GTA | TAC | AAA | TCA | CAG | ACT | CAC | ACG | GCT | GGT | CTG | GTG | 395 |
| Asp | Cys | Val | Leu | Val | Tyr | Lys | Ser | Gln | Thr | His | Thr | Ala | Gly | Leu | Val |   |
| 95 |  |  |  |  | 100 |  |  |  |  | 105 |  |  |  |  | 110 |   |
| TAC | GCT | AAA | GGT | ATC | GAC | GGG | TAT | AAG | GCT | GAA | CGT | CTG | CCG | GGT | AGT | 443 |
| Tyr | Ala | Lys | Gly | Ile | Asp | Gly | Tyr | Lys | Ala | Glu | Arg | Leu | Pro | Gly | Ser |   |
|  |  |  |  | 115 |  |  |  |  | 120 |  |  |  |  | 125 |  |   |
| TTC | CAA | GAG | GTT | CCT | AAA | GGC | GCA | CCG | CTG | CAA | GGC | TGC | TTC | ACT | ATT | 491 |
| Phe | Gln | Glu | Val | Pro | Lys | Gly | Ala | Pro | Leu | Gln | Gly | Cys | Phe | Thr | Ile |   |
|  |  |  | 130 |  |  |  |  | 135 |  |  |  |  | 140 |  |  |   |
| GAT | GAG | TTC | GGT | CGC | CGC | TGG | CAA | GTA | CAA | TAAGTGTTAA | ACTCAAGGTC |  |  |  |  | 541 |
| Asp | Glu | Phe | Gly | Arg | Arg | Trp | Gln | Val | Gln |  |  |  |  |  |  |   |
|  |  | 145 |  |  |  |  | 150 |  |  |  |  |  |  |  |  |   |

ATGCACGATG CGTGGCGGAT CGGGTACCGA GCTCGAATTC ACTGG     586

( 2 ) INFORMATION FOR SEQ ID NO:11:

( i ) SEQUENCE CHARACTERISTICS:
        ( A ) LENGTH: 152 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

|   |   |   |   |   |   |   |   |   |   |   |   |   |   |   |
|---|---|---|---|---|---|---|---|---|---|---|---|---|---|---|
| Met | Val | Phe | Thr | Lys | Glu | Pro | Ala | Asn | Val | Phe | Tyr | Val | Leu | Val | Ser |
| 1 |  |  |  | 5 |  |  |  |  | 10 |  |  |  |  | 15 |  |
| Ala | Phe | Arg | Ser | Asn | Leu | Cys | Asp | Glu | Val | Asn | Met | Ser | Arg | His | Arg |
|  |  |  | 20 |  |  |  |  | 25 |  |  |  |  | 30 |  |  |
| His | Met | Val | Ser | Thr | Leu | Arg | Ala | Ala | Pro | Gly | Leu | Tyr | Gly | Ser | Val |
|  |  | 35 |  |  |  |  | 40 |  |  |  |  | 45 |  |  |  |
| Glu | Ser | Thr | Asp | Leu | Thr | Gly | Cys | Tyr | Arg | Glu | Ala | Ile | Ser | Ser | Ala |
|  | 50 |  |  |  |  | 55 |  |  |  |  | 60 |  |  |  |  |
| Pro | Thr | Glu | Glu | Lys | Thr | Val | Arg | Val | Arg | Tyr | Lys | Asp | Lys | Ala | Gln |
| 65 |  |  |  |  | 70 |  |  |  |  | 75 |  |  |  |  | 80 |
| Ala | Leu | Asn | Val | Ala | Arg | Leu | Ala | Cys | Asn | Glu | Trp | Glu | Gln | Asp | Cys |
|  |  |  |  | 85 |  |  |  |  | 90 |  |  |  |  | 95 |  |
| Val | Leu | Val | Tyr | Lys | Ser | Gln | Thr | His | Thr | Ala | Gly | Leu | Val | Tyr | Ala |
|  |  |  | 100 |  |  |  |  | 105 |  |  |  |  | 110 |  |  |
| Lys | Gly | Ile | Asp | Gly | Tyr | Lys | Ala | Glu | Arg | Leu | Pro | Gly | Ser | Phe | Gln |
|  |  | 115 |  |  |  |  | 120 |  |  |  |  | 125 |  |  |  |
| Glu | Val | Pro | Lys | Gly | Ala | Pro | Leu | Gln | Gly | Cys | Phe | Thr | Ile | Asp | Glu |
|  | 130 |  |  |  |  | 135 |  |  |  |  | 140 |  |  |  |  |
| Phe | Gly | Arg | Arg | Trp | Gln | Val | Gln |  |  |  |  |  |  |  |  |
| 145 |  |  |  |  | 150 |  |  |  |  |  |  |  |  |  |  |

-continued ( 2 ) INFORMATION FOR SEQ ID NO:12:

( i ) SEQUENCE CHARACTERISTICS:
        ( A ) LENGTH: 2216 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Fig. 13, E8 promoter ( x i ) SEQUENCE DESCRIPTION: SEQ ID NO:12:

```
GAATTCATTT  TTGACATCCC  TAATGATATT  GTTCACGTAA  TTAAGTTTTG  TGGAAGTGAG      60
AGAGTCCAAT  TTTGATAAGA  AAAGAGTCAG  AAAACGTAAT  ATTTTAAAAG  TCTAAATCTT     120
TCTACAAATA  AGAGCAAATT  TATTTATTTT  TAATCCAAT   AAATATTAAT  GGAGGACAAA     180
TTCAATTCAC  TTGGTTGTAA  AATAAACTTA  AACCAATAAC  CAAAGANCTA  ATAAATCTGA     240
AGTGGAATTA  TTAAGGATAA  TGTACATAGA  CAATGAAGAA  ATAATAGGTT  CGATGAATTA     300
ATAATAATTA  AGGATGTTAC  AATCATCATG  TGCCAAGTAT  ATACACAATA  TTCTATGGA      360
TTTATAATTT  CGTTACTTCA  CTTAACTTTT  GCGTAAATAA  AACGAATTAT  CTGATATTTT     420
ATAATAAAAC  AGTTAATTAA  GAACCATCAT  TTTAACAAC   ATAGATATAT  TATTTCTAAT     480
AGTTTAATGA  TACTTTTAAA  TCTTTTAAAT  TTTATGTTTC  TTTAGAAAA   TAAAAATTCA     540
AAAAAATTAA  ATATATTTAC  AAAAACTACA  ATCAAACACA  ACTTCATATA  TTAAAAGCAA     600
AATATATTTT  GAAAATTTCA  AGTGTCCTAA  CAAATAAGAC  AAGAGGAAAA  TGTACGATGA     660
GAGACATAAA  GAGAACTAAT  AATTGAGGAG  TCCTATAATA  TATAATAAAG  TTTATTAGTA     720
AACTTAATTA  TTAAGGACTC  CTAAATATA   TGATAGGAGA  AAATGAATGG  TGAGAGATAT     780
TGGAAAACTT  AATAATTAAG  GATNTAAAA   TATATGGTAA  AAGATAGGCA  AAGTATCCAT     840
TATCCCCTTT  TAACTTGAAG  TCTACCTAGG  CGCATGTGAA  AGGTTGATTT  TTGTCACGT      900
CATATAGCTA  TAACGTAAAA  AAAGAAAGTA  AAATTTTTAA  TTTTTTTTAA  TATATGACAT     960
ATTTTAAACG  AAATATAGGA  CAAAATGTAA  ATGAATAGTA  AAGGAAACAA  AGATTAATAC    1020
TTACTTTGTA  AGAATTTAAG  ATAAATTTAA  AATTTAATAG  ATCAACTTTA  CGTCTAGAAA    1080
GACCCATATC  TAGAAGGAAT  TTCACGAAAT  CGGCCCTTAT  TCAAAATAA   CTTTTAAATA    1140
ATGAATTTTA  AATTTTAAGA  AATAATATCC  AATGAATAAA  TGACATGTAG  CATTTTACCT    1200
AAATATTTCA  ACTATTTTAA  TCCAATATTA  ATTTGTTTTA  TTCCCAACAA  TAGAAAGTCT    1260
TGTGCAGACA  TTTAATCTGA  CTTTTCCAGT  ACTAAATATT  AATTTTCTGA  AGATTTTCGG    1320
GTTAGTCCA   CAAGTTTTAG  TGAGAAGTTT  TGCTCAAAAT  TTAGGTGAG   AAGGTTTGAT    1380
ATTTATCTTT  TGTTAAATTA  ATTTATCTAG  GTGACTATTA  TTTATTTAAG  TAGAAATTCA    1440
TATCATTACT  TTTGCCAACT  TGTAGTCATA  ATAGGAGTAG  GTGTATATGA  TGAAGGAATA    1500
AACAAGTTCA  GTGAAGTGAT  TAAAATAAAA  TATAATTTAG  GTGTACATCA  AATAAAAACC    1560
TTAAAGTTTA  GAAAGGCACC  GAATAATTTT  GCATAGAAGA  TATTAGTAAA  TTTATAAAAA    1620
TAAAAGAAAT  GTAGTTGTCA  AGTTGTCTTC  TTTTTTTTGG  ATAAAAATAG  CAGTTGGCTT    1680
ATGTCATTCT  TTTACAACCT  CCATGCCACT  TGTCCAATTG  TTGACACTTA  ACTAATTAGT    1740
TTGATTCATG  TATGAATACT  AAATAATTTT  TTAGGACTGA  CTCAAATATT  TTATATTAT    1800
CATAGTAATA  TTTATCTAAT  TTTAGGACC   ACTTATTACT  AAATAATAAA  TTAACTACTA    1860
```

-continued

| | | | | | | |
|---|---|---|---|---|---|---|
| CTATATTATT | GTTGTGAAAC | AACAACGTTT | TGGTTGTTAT | GATGAAACGT | ACACTATATC | 1920 |
| AGTATGAAAA | ATTCAAAACG | ATTAGTATAA | ATTATATTGA | AAATTTGATA | TTTTTCTATT | 1980 |
| CTTAATCAGA | CGTATTGGGT | TTCATATTTT | AAAAGGGAC | TAAACTTAGA | AGAGAAGTTT | 2040 |
| GTTGAAACT | ACTTTTGTCT | CTTTCTTGTT | CCCATTTCTC | TCTTAGATTT | CAAAAAGTGA | 2100 |
| ACTACTTTAT | CTCTTTCTTT | GTTCACATTT | TATTTTATTC | TATTATAAAT | ATGGCATCCT | 2160 |
| CATATTGAGA | TTTTTAGAAA | TTATTCTAAT | CATTCACAGT | GCAAAAGACC | ATGGAA | 2216 |